(12) United States Patent
Stark

(10) Patent No.: US 9,314,232 B2
(45) Date of Patent: Apr. 19, 2016

(54) TOOLS FOR PERFORMING LESS INVASIVE ORTHOPEDIC JOINT PROCEDURES

(75) Inventor: John G. Stark, Deephaven, MN (US)

(73) Assignee: Ilion Medical, Inc, Minneapolis, MN (US)

( * ) Notice: Subject to any disclaimer, the term of this patent is extended or adjusted under 35 U.S.C. 154(b) by 0 days.

(21) Appl. No.: 13/529,123

(22) Filed: Jun. 21, 2012

(65) Prior Publication Data

US 2012/0316565 A1    Dec. 13, 2012

Related U.S. Application Data

(63) Continuation of application No. 12/072,694, filed on Feb. 27, 2008.

(51) Int. Cl.

| A61B 17/17 | (2006.01) |
|---|---|
| A61B 17/02 | (2006.01) |
| A61B 17/88 | (2006.01) |
| A61B 17/86 | (2006.01) |
| A61B 17/00 | (2006.01) |
| A61B 19/00 | (2006.01) |

(Continued)

(52) U.S. Cl.
CPC ......... *A61B 17/025* (2013.01); *A61B 17/1757* (2013.01); *A61B 17/885* (2013.01); *A61B 17/866* (2013.01); *A61B 2017/00004* (2013.01); *A61B 2017/0256* (2013.01); *A61B 2019/304* (2013.01); *A61F 2002/30622* (2013.01); *A61F 2002/4658* (2013.01)

(58) Field of Classification Search
CPC .................................................. A61B 17/1761
USPC ........................................ 606/80, 90, 96, 99
See application file for complete search history.

(56) References Cited

U.S. PATENT DOCUMENTS

| 3,867,932 A | * | 2/1975 | Huene ............................. 606/80 |
| 4,488,542 A | | 12/1984 | Helland |
| 4,512,344 A | | 4/1985 | Barber |

(Continued)

FOREIGN PATENT DOCUMENTS

| JP | 10-000200 A | 1/1998 |
| JP | 11-076247 A | 3/1999 |

(Continued)

OTHER PUBLICATIONS

Presentation by Dr. John G. Stark, Minnesota Orthopedic Society, Eighteenth Annual Meeting, May 2002.

(Continued)

*Primary Examiner* — Samuel Hanna
(74) *Attorney, Agent, or Firm* — Dardi & Herbert, PLLC; Peter S. Dardi

(57) ABSTRACT

A tool set for preparing a joint, inserting an implant or removing an implant from a joint in an open or less invasive procedure generally comprises a set of nested tools, pin guides, jigs, and/or immobilization elements. The nested tool set comprises at least one pin and at least one cannulated tool. The cannula can comprise tangs that project from the distal end of the cannula. The tangs can be offset such that drilling removes different amounts of bone relative to drilling through a centered drill guide. The cannulated tool kit can comprise at least one tool guide/cannula, drill bits/reamer, syringe, and/or inserter. At least one cannula is positioned over and around the pin position into the joint. The channel of the cannula guides the other tools into the joint.

20 Claims, 10 Drawing Sheets

(51) Int. Cl.
*A61F 2/30* (2006.01)
*A61F 2/46* (2006.01)

(56) References Cited

U.S. PATENT DOCUMENTS

| | | |
|---|---|---|
| 4,569,338 A | 2/1986 | Edwards |
| 4,590,928 A | 5/1986 | Hunt et al. |
| 4,640,271 A | 2/1987 | Lower |
| 4,772,287 A | 9/1988 | Ray et al. |
| 4,950,270 A | 8/1990 | Bowman et al. |
| 4,961,740 A | 10/1990 | Ray et al. |
| 5,015,247 A | 5/1991 | Michelson |
| 5,226,766 A | 7/1993 | Lasner |
| 5,242,444 A | 9/1993 | MacMillan |
| 5,294,227 A | 3/1994 | Forster et al. |
| 5,295,980 A | 3/1994 | Ersek |
| 5,334,205 A | 8/1994 | Cain |
| 5,336,225 A | 8/1994 | Zang |
| 5,341,816 A | 8/1994 | Allen |
| 5,368,593 A | 11/1994 | Stark |
| 5,443,509 A | 8/1995 | Boucher et al. |
| 5,456,267 A | 10/1995 | Stark |
| 5,470,334 A | 11/1995 | Ross et al. |
| 5,492,442 A | 2/1996 | Lasner |
| 5,607,432 A | 3/1997 | Fucci |
| 5,669,909 A | 9/1997 | Zdeblick et al. |
| 5,690,677 A | 11/1997 | Schmieding et al. |
| 5,741,253 A | 4/1998 | Michelson |
| 5,741,261 A | 4/1998 | Moskovitz et al. |
| 5,743,914 A | 4/1998 | Skiba |
| 5,772,594 A | 6/1998 | Barrick |
| 5,772,661 A * | 6/1998 | Michelson .................. 606/86 A |
| 5,797,909 A | 8/1998 | Michelson |
| 5,865,847 A | 2/1999 | Kohrs et al. |
| 5,871,486 A | 2/1999 | Huebner et al. |
| 5,919,193 A | 7/1999 | Slavitt |
| 5,928,239 A | 7/1999 | Mirza |
| 5,964,768 A | 10/1999 | Huebner |
| 5,993,463 A | 11/1999 | Truwit |
| 6,030,162 A | 2/2000 | Huebner |
| 6,053,916 A | 4/2000 | Moore |
| 6,162,053 A | 12/2000 | Hollander |
| 6,175,758 B1 | 1/2001 | Kambin |
| 6,180,606 B1 | 1/2001 | Chen et al. |
| 6,210,412 B1 * | 4/2001 | Michelson .................. 606/86 A |
| 6,224,607 B1 | 5/2001 | Michelson |
| 6,270,498 B1 | 8/2001 | Michelson |
| 6,283,966 B1 | 9/2001 | Houfburg |
| 6,290,724 B1 | 9/2001 | Marino |
| 6,294,187 B1 | 9/2001 | Boyce et al. |
| 6,306,170 B2 | 10/2001 | Ray |
| 6,351,573 B1 | 2/2002 | Schneider |
| 6,375,657 B1 | 4/2002 | Doubler et al. |
| 6,402,785 B1 | 6/2002 | Zdeblick et al. |
| 6,479,633 B1 | 11/2002 | Ni et al. |
| 6,540,752 B1 | 4/2003 | Hicken et al. |
| 6,562,046 B2 | 5/2003 | Sasso |
| 6,562,049 B1 | 5/2003 | Norlander et al. |
| 6,595,995 B2 | 7/2003 | Zdeblick et al. |
| 6,607,487 B2 | 8/2003 | Chang et al. |
| 6,635,059 B2 | 10/2003 | Randall et al. |
| 6,660,007 B2 | 12/2003 | Khanna |
| 6,666,888 B1 | 12/2003 | Jackson |
| 6,746,451 B2 | 6/2004 | Middleton et al. |
| 6,807,885 B2 | 10/2004 | Loper |
| 6,827,722 B1 * | 12/2004 | Schoenefeld ................. 606/104 |
| 6,875,215 B2 | 4/2005 | Taras et al. |
| 6,984,235 B2 | 1/2006 | Huebner |
| 7,001,393 B2 | 2/2006 | Schwenke et al. |
| 7,083,647 B1 | 8/2006 | Sklar et al. |
| RE40,796 E * | 6/2009 | O'Neill ......................... 600/567 |
| 2001/0053914 A1 | 12/2001 | Landry et al. |
| 2002/0082704 A1 * | 6/2002 | Cerundolo .................. 623/20.35 |
| 2002/0087161 A1 | 7/2002 | Randall et al. |
| 2002/0099288 A1 | 7/2002 | Chang et al. |
| 2002/0099385 A1 * | 7/2002 | Ralph et al. .................... 606/92 |
| 2002/0116006 A1 * | 8/2002 | Cohen ............................ 606/99 |
| 2002/0143343 A1 | 10/2002 | Castro |
| 2002/0147498 A1 * | 10/2002 | Tallarida et al. ............ 623/20.14 |
| 2002/0183846 A1 | 12/2002 | Kuslich et al. |
| 2003/0032098 A1 | 2/2003 | Young et al. |
| 2003/0144736 A1 | 7/2003 | Sennett |
| 2003/0158553 A1 * | 8/2003 | Michelson ...................... 606/61 |
| 2004/0215198 A1 | 10/2004 | Marnay et al. |
| 2004/0228901 A1 | 11/2004 | Trieu et al. |
| 2004/0267365 A1 | 12/2004 | Fornari |
| 2005/0021041 A1 | 1/2005 | Michelson |
| 2005/0038513 A1 | 2/2005 | Michelson |
| 2005/0137602 A1 | 6/2005 | Assell et al. |
| 2006/0058793 A1 | 3/2006 | Michelson |
| 2006/0074434 A1 | 4/2006 | Wenstrom, Jr. et al. |
| 2006/0074445 A1 * | 4/2006 | Gerber et al. ................. 606/191 |
| 2006/0084992 A1 | 4/2006 | Michelson |
| 2006/0085006 A1 * | 4/2006 | Ek et al. ......................... 606/86 |
| 2006/0085068 A1 * | 4/2006 | Barry ......................... 623/17.11 |
| 2006/0089646 A1 | 4/2006 | Bonutti |
| 2006/0111782 A1 | 5/2006 | Petersen |
| 2006/0129238 A1 | 6/2006 | Paltzer |
| 2006/0190001 A1 | 8/2006 | Powell |
| 2006/0200138 A1 * | 9/2006 | Michelson ...................... 606/61 |
| 2006/0200139 A1 | 9/2006 | Michelson |
| 2006/0224240 A1 | 10/2006 | Allard et al. |
| 2006/0235522 A1 | 10/2006 | Foley |
| 2007/0027543 A1 | 2/2007 | Gimble et al. |
| 2007/0032875 A1 | 2/2007 | Blacklock et al. |
| 2007/0055374 A1 | 3/2007 | Copf, Jr. et al. |
| 2007/0118143 A1 * | 5/2007 | Ralph et al. .................... 606/92 |
| 2007/0156241 A1 | 7/2007 | Reiley et al. |
| 2007/0239160 A1 * | 10/2007 | Zipnick et al. ................. 606/61 |
| 2008/0009861 A1 | 1/2008 | Stark |
| 2008/0195103 A1 * | 8/2008 | Lawis et al. .................... 606/80 |
| 2008/0249627 A1 | 10/2008 | Moehlenbruck et al. |
| 2009/0024174 A1 | 1/2009 | Stark |
| 2009/0099610 A1 | 4/2009 | Johnson et al. |
| 2009/0259261 A1 | 10/2009 | Reiley |

FOREIGN PATENT DOCUMENTS

| | | |
|---|---|---|
| WO | 9535180 | 12/1995 |
| WO | 99/52453 A2 | 10/1999 |
| WO | 2007/057928 A1 | 5/2007 |
| WO | 2008011410 | 1/2008 |

OTHER PUBLICATIONS

Wise et al., "Minimally Invasive Sacroiliac Arthrodesis Outcomes of a New Technique" J. Spinal Discord Tech., 21 (8):579-584, (2008).
International Search Report and Written Opinion for International Application No. PCT/US2009/001198, dated Sep. 30, 2009.
Synthes (USA) "4.5 mm Cannulated Screw Technique Guide," 1995.
Supplementary European Search Report for co-pending European Application No. 09715842.2 dated Nov. 16, 2012 (5 pages).
Office Action from co-pending Japanese application No. 2010-548712 dated Mar. 5, 2013 (7 pages).
European search report for co-pending application No. 14196573.1 dated Mar. 11, 2015 (7 pages.)

* cited by examiner

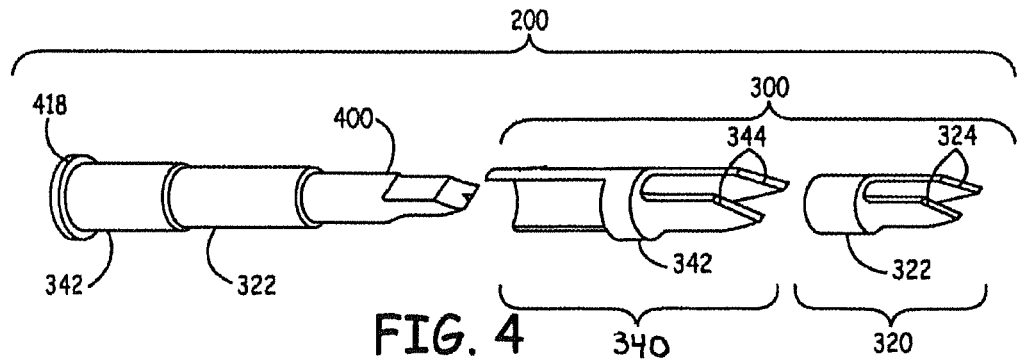
FIG. 4
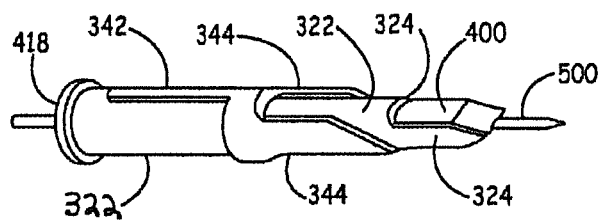
FIG. 5
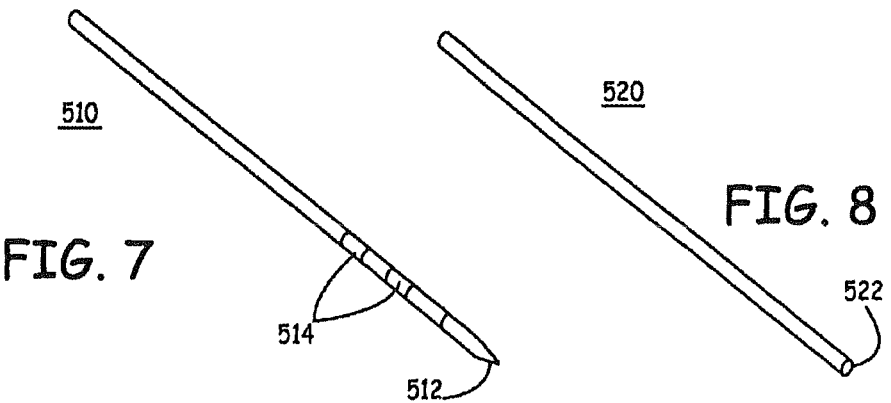
FIG. 7
FIG. 8

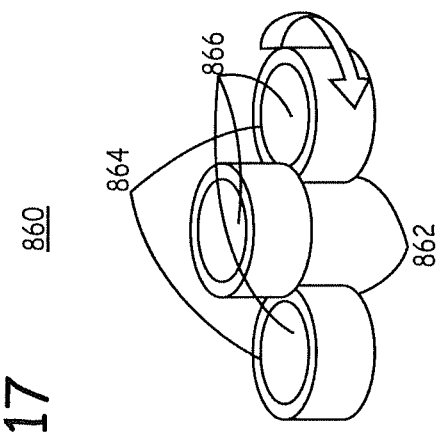
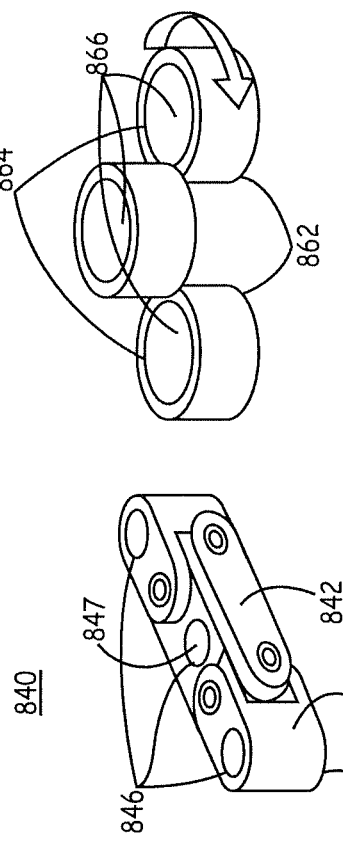
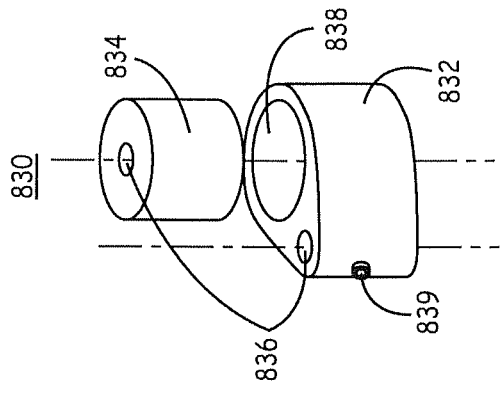
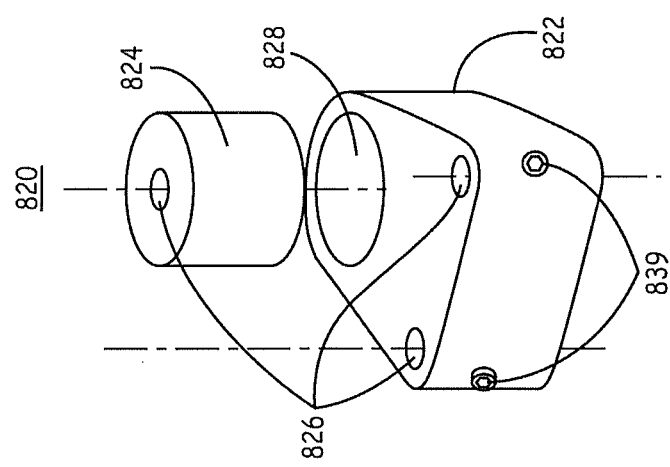
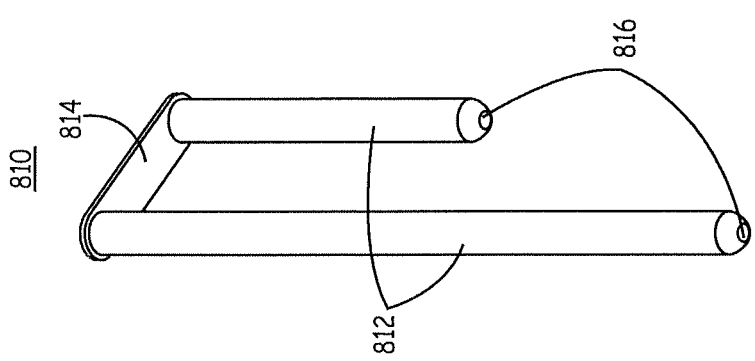

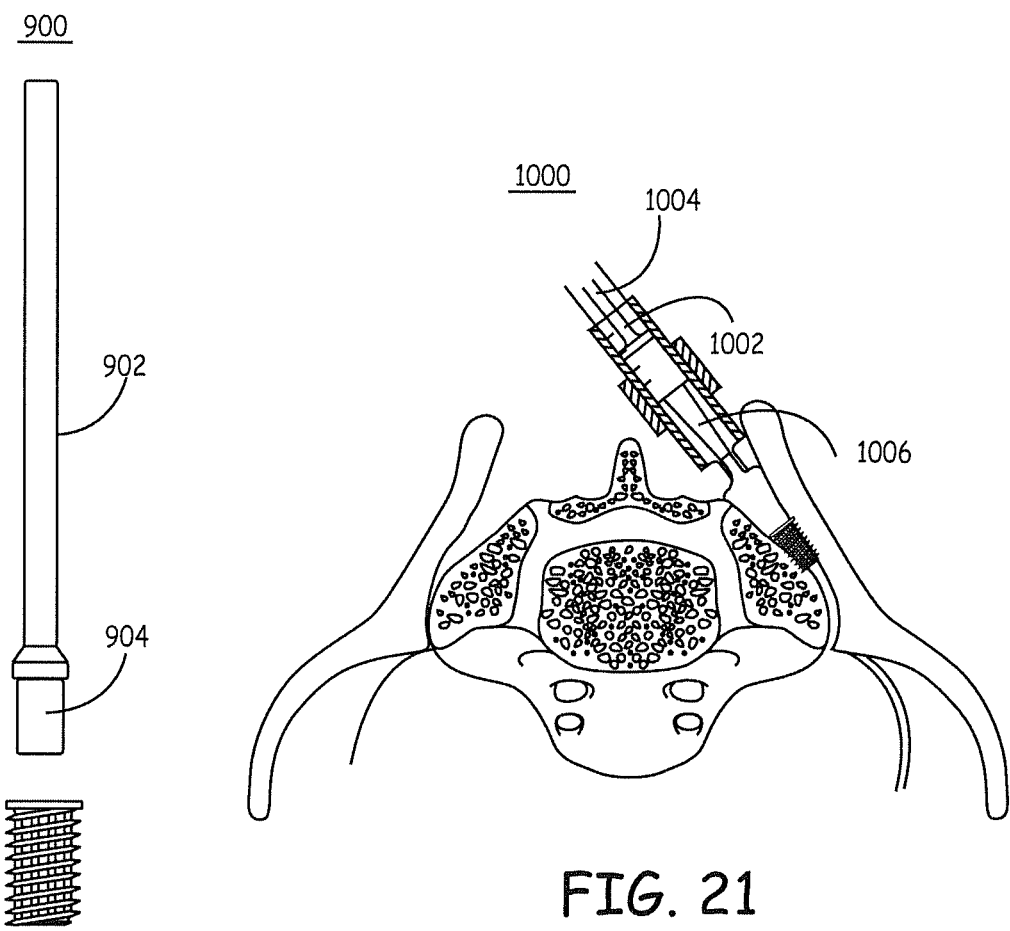

TOOLS FOR PERFORMING LESS INVASIVE ORTHOPEDIC JOINT PROCEDURES

CROSS REFERENCE TO RELATED APPLICATIONS

This patent application is a continuation of copending U.S. patent application Ser. No. 12/072,694 filed on Feb. 27, 2008 to Stark, entitled "Tools For Performing Less Invasive Orthopedic Joint Procedures," incorporated herein by reference.

FIELD OF THE INVENTION

The invention relates to less invasive approaches for the immobilization or fusion of joints, such as the sacroiliac joint, and apparatuses for facilitating the procedures.

BACKGROUND OF THE INVENTION

Lower back pain is a common ailment among the population and results in pain and suffering as well as loss of work time. Thus, approaches for the treatment of back pain can both relieve suffering as well as reduce employee sick time. Since back pain results in considerable employee absenteeism, effective treatments for lower back pain have both economic benefits as well as the benefit of alleviating considerable suffering. In some cases, back pain can be alleviated through the fusion of adjacent bones, such as vertebrae.

The sacroiliac joint is located at the juncture of the ilium, the upper bone of the pelvis, and the sacrum at the base of the spine. While the sacroiliac joint has a limited range of motion, dysfunction of the joint has been identified. The joint is supported by a range of ligaments including, for example, the sacroiliac ligament at the base of the joint and the anterior sacroiliac ligament at the top of the joint. The joint is in the vicinity of the passage of a large number of blood vessels and nerves that pass from the torso to the lower extremities. Any procedures near the joint should avoid damage to significant adjacent vessels and nerves.

SUMMARY OF THE INVENTION

In a first aspect, the invention pertains to an orthopedic drill guide comprising a body portion and a plurality of projections. The body portion has a first end and a second end and forms a drill channel. The plurality of projections extends from the second end of the body portion and can be asymmetrically distributed relative to the drill.

In a second aspect, the invention pertains to a set of tools for performing an orthopedic procedure comprising a first pin, a cannula, and a form. The cannula comprises projections extending from an edge of the cannula and a drill channel extending along a length of the cannula. The form comprises a bore that has a size to receive the pin and an outer surface that that fits within the drill channel of the cannula. The form has a shaped tip. In some embodiments, the shaped tip forms an approximately continuous pointed tip with the projections of the cannula. In additional embodiments, the shaped tip comprises spiral threads along a tapered tip.

In a third aspect, the invention pertains to a method for preparing an orthopedic joint for the placement of an implant into the joint, such as between the ilium and the sacrum though an extra-articular recess. The method comprises cutting a passageway into the joint using a drill guide that is positioned asymmetrically relative to the center of the joint.

In a fourth aspect, the invention pertains to a method for placing an implant into a joint, such as between the ilium and the sacrum through an extra-articular recess. The method comprises preparing the joint for the placement of the implant and inserting an implant into the drilled region. Preparing the joint for placement of the implant involves cutting a passageway into the sacroiliac joint using a drill guide that is positioned asymmetrically relative to the center of the joint.

In a fifth aspect, the invention pertains to a method for preparing a sacroiliac joint for the placement of an implant into the joint between the ilium and the sacrum through an extra-articular recess. The method comprises cutting bone to form an implant position for placement of an implant. The cutting is performed with a drill bit placed through a cannula comprising projections extending from an end of the cannula into the space of the joint.

In a sixth aspect, the invention pertains to a method for preparing for the insertion of a plurality of implants into a sacroiliac joint between an ilium and a sacrum through an extra-articular recess using a drill guide comprising a plurality of bores. The method comprises creating a plurality of passageways into the sacroiliac joint by inserting a cannula comprising a channel over pins in different bores of the positioned drill guide. The plurality of bores is spaced in preselected amounts for spacing the implants in preselected amounts in the sacroiliac joint.

In a further aspect, the invention pertains to a cannulated inserter comprising a shaft, a handle and a gripping element. In general, the shaft connects the handle and the gripping element. The inserter can comprise a channel extending along the length of the inserter, and the gripping element can be configured to releasably grip an orthopedic insert.

In another aspect, the invention pertains to a method for preparing a joint for placement of an implant into, or extraction of an implant from, a joint, the method comprising placing a set of nested cannulae into a patient. The cannulae can comprise projections from a tip of each cannula that are inserted into the joint. In some embodiments, at least an inner cannula further comprises a connection for a releasable handle near a proximal end of the inner cannula. The inner cannulae can slide effectively freely within an outer cannula such that the inner cannula can be removed to provide the larger inner space of the outer cannula for the performance of a procedure at the joint.

BRIEF DESCRIPTION OF THE DRAWINGS

FIG. 4 is a perspective view of a nested tool set with the tools in a cut away exploded view in which outer elements are cut and pulled away to expose the relationship of the elements.

FIG. 5 is another perspective view of a nested tool set with the tools part way assembled and with portions of an outer cannula removed for viewing purposes.

FIG. 7 is a side view of a pointed tip pin with incremental markings.

FIG. 8 is a side view of a ball tip pin without incremental markings.

FIG. 15 is a perspective view of a "gunsight" jig for inserting multiple pins into a joint.

FIG. 16 is a perspective view of a jig with three holes for inserting a single implant into the sacroiliac joint with the jig secured in position.

FIG. 17 is a perspective view of an alternative embodiment of a jig for the placement of a single implant into the sacroiliac joint.

FIG. 18 is a perspective view of an embodiment of a jig for inserting multiple implants at selected positions into a joint.

FIG. 19 is a perspective view of a third embodiment of a jig for inserting multiple implants into a joint.

FIG. 20 is a side view of a cannulated inserter for inserting an implant within a joint.

FIG. 21 is a side view of a syringe for applying a filler material within a joint.

DETAILED DESCRIPTION OF THE INVENTION

Figure 1:
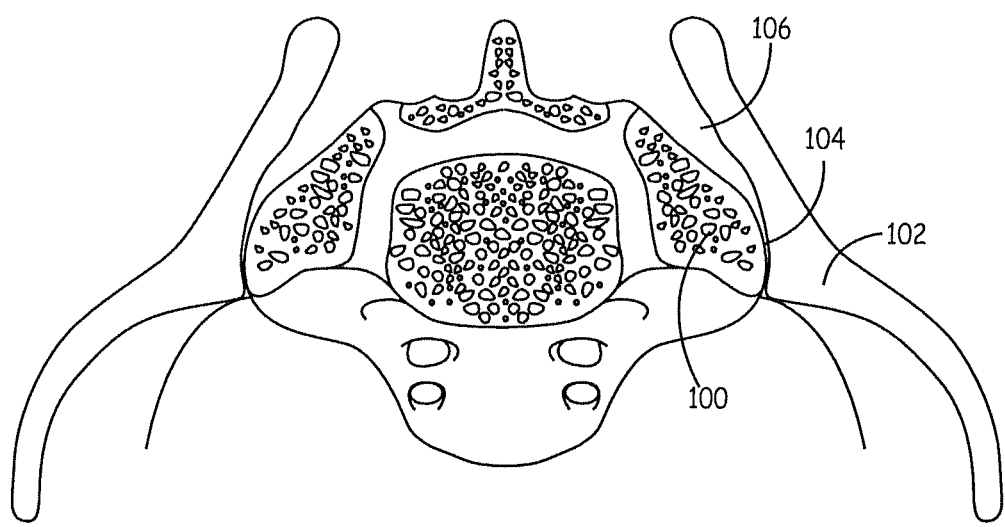
FIG. 1 is a sectional view of the sacroiliac joint taken across a person's torso.

It has been discovered that immobilization or fusion of the sacroiliac joint can result in significant relief of lower back pain for patients in which injury or disease of the joint is resulting in the pain. Improved tools are described herein for performing the approach, preparation and/or immobilization of the sacroiliac joint using less invasive procedures through small incisions to provide limited, but appropriate, access to the joint. These tools can be adapted for procedures in other joints, such as spinal procedures at the joining of two vertebrae. In particular, less invasive procedures can be performed to place implants within the joint to achieve the desired immobilization and/or biological treatment, which can ultimately result in joint fusion. In some embodiments, a set of cannulated nested tools can be used to efficiently and safely locate the joint, expose a location in the joint, prepare the joint and provide for placement of an implant and/or other treatment/immobilization materials. The tools can generally be guided over a pin and/or within a cannula to guide tools to the selected location within the joint. Cannulae can be designed to engage the joint in a shifted configuration such that the sacroiliac joint can be drilled to remove relatively more bone material from the ilium relative to the amount of bone to be removed form the sacrum or correspondingly from other bones for different joints. Jigs can be used to support the entry point for the procedure and/or to align the placement of multiple implants along the joint, which can each be performed using the nested tool sets. In some embodiments, the set of nested tools can be telescoped over each other with releasable handles providing for selective placement and manipulation of the individual cannulated tools appropriately nested with a pin and a cannula directing the tool, although alternative embodiments and details on individual improved tools are described in the following discussion.

Various devices, such as bolts, nails, screws, agglomerated inorganic and/or organic materials, and the like, can be used as treatment and/or immobilization elements. Such devices can be further used with one or more biologically active agents. Implants are also described in the present inventor's copending U.S. patent application Ser. No. 11/879,536, filed on Jul. 17, 2007, entitled "Bone Screws and Particular Applications to Sacroiliac Joint Fusion" and copending U.S. Patent Application Publication number 2008/0009861, filed on Mar. 10, 2004, entitled "Sacroiliac Joint Immobilization," both of which are incorporated herein by reference.

Immobilization of the sacroiliac joint, spine or other joint generally can involve placement of an immobilization element or structure within the joint through the gap or opening of the joint, e.g., between the ilium and the sacrum. The opening of the sacroiliac joint can be approached through an incision in the patient's back to provide an approach with less risk of damaging nerves and blood vessels passing from the torso to the lower extremities. It is believed that joint contact between worn or damaged section(s) of the joint can result in pain. Placement of an implant into the joint distracts the joint while tending to immobilize the joint by pushing outward on resisting ligaments, which is in contrast with bolting the sacroiliac joint to compress the joint, which may unload or relax the ligaments. Surgical procedures have demonstrated that for many patients the pain can be resolved by immobilization with distraction of the joint. Hundreds of successful open procedures have been performed to alleviate pain through sacroiliac joint fusion. The joint can be examined to determine whether immobilization or other form of treatment is desired. While the discussion herein focuses on procedures relating to the sacroiliac joint, the tools and procedures can be generalized for other joints based on the teachings herein.

In general, the immobilization can be performed either by a surgical procedure to expose the appropriate sections of the joint or through less invasive approaches in which tools and implants are introduced to the region through a cannula or the like. In any case, immobilization of the joint involves identifying appropriate locations to place the immobilization elements. Once the appropriate locations are identified, the locations can be exposed in an open procedure or located, such as with pins, in a less invasive or closed procedure, and the immobilization elements are appropriately placed. Drilling, chiseling, tapping and/or scraping generally can be used to prepare the joint and to facilitate the placement of the immobilization elements. In particular, drill guides or the like can be used in open and/or less invasive, i.e., close procedures, to drill out or otherwise prepare or decorticate the bone. Preparation of the bone at the implant site provides appropriate surface area for the placement and efficacy of the immobilization implant and/or material as well as stimulating bone growth and healing that further contributes to fusion of the joint upon healing of the wound.

For less invasive procedures, placement of immobilization elements at one point within the joint generally involves the use of a plurality of tools that can be delivered into the joint through a small incision. The tools are guided to the selected location in joint through a cannula and/or over a pin. Thus, the tools generally are designed with a low radial profile to fit within the space available within the cannula. The set of tools can function in a nested configuration to efficiently function in the small available space. In general, kits or tool sets can comprise, for example, one or more of the following: alignment components, guiding components, cutting components, delivery components and jigs. Alignment components can include, for example, one or more pins, pin guides (e.g. depth guides) and sizers. Guiding components can comprise one or more cannula and fillers that support the cannula during insertion. Cutting components can comprise one or more drill bits or the like. Delivery components can include, for example, one or more inserters that facilitate placement of an implant and syringes that can be used to deliver biologics or the like. Jigs can be stabilized with pins to stabilize the entry point for the less invasive procedure. In some embodiments, each of the nested tools is cannulated such that the tool comprises a channel that receives the pin to ensure that the tool is positioned in a specific location marked by the pin. After the pin is positioned, one or a plurality of cannulae can be inserted over the pin to provide a stable opening to the selected position in the joint. The cannula comprises an inner lumen for receiving subsequent tools as well as an outer surface that can interface with larger tools, such as a larger diameter cannula.

In some embodiments, improved cannulae have one or more projections or tangs extending from the tip or distal edge of a cannula to extend into the joint. In particular, a cannula can have two or more projections distributed to fix a cannula relative to the joint while providing an open channel to the joint, and these cannulae with projections can be referred to as anchoring cannulae. With two projections sticking into the joint, the orientation of the cannula relative to the joint is more secure. In some embodiments, the projections can be placed on the edge of the cannula such that the center of the channel is not centered over the joint. Using an uncentered or shifted cannula for preparation and immobilization of the joint can take advantage of the asymmetric properties of the bones at the joint with respect to geometry, hardness, combinations thereof and the like. In some embodiments, with the use of the asymmetric projections, an increased amount of bone from one side of the joint can be removed relative to the opposing surface of the joint and the implant correspondingly has a greater amount of surface area in contact with bone having a greater amount of bone removed. Thus, in some embodiments, a relatively greater amount of bone is removed from the ilium relative to the sacrum when using a cannula with asymmetric projections, although since the ilium is harder, the drill guide also improves consistency with respect to drilling an appropriate amount into the ilium, even if quantification of the actual amounts of bone removal is elusive. Thus, the drill guide with asymmetric projections facilitates the desired preparation of the joint for placement of immobilization elements.

In some embodiments, a set of nested cannulae can be used. The outer cannula clearly has a larger inner diameter than an inner cannula. Thus, during the procedure, an inner cannula can be removed to provide more space for the procedure. More space may be desirable for different portions of a procedure and/or as a result of a decision during a procedure to use a larger implant. Placement and selective removal of nested cannulae can be performed efficiently with appropriate tool design. In some embodiments, the cannulae have essentially smooth surfaces without significant discontinuities so that the nested cannula can easily slide onto and off from each other. However, the cannulae can have inner threads, outer threads and/or another type of connector, such as a bayonet type connector, near the proximal ends to provide for attachment of a handle to facilitate handling of the element. One or more of the nested cannulae can have projections for anchoring the cannulae in the joint, and the prongs may be positioned to shift the center of the cannulae away from the center of the joint.

Generally, to perform the less invasive procedure, a pin, for example, a blunt pin, is inserted into the joint, e.g., sacroiliac joint, such as with the help of imaging. The pin can be used to guide a series of cannulated instruments into the joint. A blunt pin can be replaced during the procedure with a sharp pin that can be placed safely deeper into the joint once the position of the initial pin is checked with imaging. Each of the cannulated instruments comprises a channel that receives the pin. One or a plurality of cannulae can be placed based on the positioning of the pin and provides access to the sacroiliac joint. In some embodiments, the cannulae can be delivered over a sizer to facilitate a desirable orientation into the joint. Additional steps of the procedure can be performed within the central lumen of a cannula, including, for example, cutting a passageway into the joint for the implant and placing the implant and filler material into the joint. Cutting tools for creating the passageway and inserters and syringes for placing the implant and material can be guided into the joint, e.g., the sacroiliac joint, by being inserted over the pin and within the cannula. In some embodiments, the pin can be removed with the cannula in position, such that the cannula provides guidance to the joint.

To place additional implants, this procedure can be repeated. For example, for immobilization of the sacroiliac joint, the initial implant location can be displaced a selected distance generally from about 10 to about 25 mm from the center of the initial implant between pins marking the edges of the joint along a patient's back. In some embodiments, the relative positioning of additional implants and corresponding tools may be aided by jigs that are designed to orient several implantation procedures based on the structure of the jig. The jigs can be used to place multiple pins and/or multiple cannulated tools into the joint sequentially or with procedures overlapping in time. In general, a plurality of implants can be used to immobilize the joint, such as two implants, three implants or more than three implants.

A wide range of immobilization elements is suitable for immobilizing the joint, e.g., SI joint, either alone or in combination. For example, the immobilization element can be a nail, a screw, a dart, a wedge, a shim, a cage, agglomerated inorganic and/or organic material, or the like or combinations thereof. Screws can be effectively used based anchoring the screw within the joint. Suitable screws can be solid, cannulated or hollow, although hollow screws can facilitate bone in-growth and may contain other elements such as biological agents that can further stimulate bone in-growth. The threads of the screw grip the bone on either side of the joint to further the immobilization of the joint. Thus, screws with sharp and/or pointed threads can be effective. Similarly, a non-uniform thread can improve the gripping while providing for effective implantation of the screw. In some embodiments, a screw can be tapered along the threads by about 2 degrees to about 10 degrees or more to facilitate implantation and/or the gripping function. A self-tapping screw with one or more flutes or the like can be used, such that pre-drilling or tapping may not be used.

Implantation elements can be formed, for example, from biocompatible material. Biocompatible metals, polymers, and/or composites, for example, can be effectively used. In particular, titanium elements generally yield desirable results for interfacing with bones. Similarly, metal powder, such as powders of titanium or titanium compositions with appropriate particle size, can be formed into composites with polymers to form desired immobilization elements. In addition, synthetic bone materials and/or sterile bone materials, either allograft or xenograft materials, can be used to form the implantation elements. Suitable synthetic bone material includes, for example, coral and calcium compositions, such as hydroxyapatite, calcium phosphate and calcium sulfate. Bone material can also be placed into other areas of the joint separately to further stimulate bone growth that can lead to fusion of the bone in the post operation period.

The immobilization elements can further comprise one or more biologically active agents that facilitate the stabilization of the immobilized joint. For example, the biologically active agent can be coated onto the exterior of the immobilization element and/or applied for gradual release such as by blending in a bioresorbable polymer that releases the biologically active agent or agents in an appropriate time dependent fashion as the polymer degrades within the patient. Furthermore, bioactive agents can be placed directly into the incision using a suitable carrier and/or support material to stimulate desired healing processes. Suitable biologically active agents include, for example, bone growth stimulating agents, such as bone morphogenic protein (BMP) and suitable cytokines. BMP mediates the formation and healing of bone, cartilage, tendon and other bone related tissues. One human BMP polypeptide is described in detail in Published U.S. Patent Application Serial Number 2003/032098 to Young et al., entitled "Bone Morphogenic Protein," incorporated herein by reference. Similarly, cytokines can be effective to stimulate bone marrow growth. A human cytokine, human chemokine alpha 2, is described in U.S. Pat. No. 6,479,633 to Ni et al., entitled "Chemokine Alpha 2," incorporated herein by reference.

For either more open techniques and/or less invasive techniques, one or more immobilization points can be identified, for example, from an image using x-ray or other imaging technique, based on appropriate positioning of the adjacent bones and appropriate anchoring to effect the immobilization and ligamentotaxis. Once the points are identified, one or more guide pins may or may not be used to mark the immobilization points as well as the ends of the joint along the patient's back. If guide pins are used, they can be inserted into position to guide drilling and/or placement of immobilization elements. X-rays can be taken with the guide pins in place to verify proper placement. Also, x-rays and/or other imaging approaches can be used before and/or during pin placement for virtual imaging. Placement of a guide based on a CT image for back surgery is described in U.S. Pat. No. 6,175,758 to Kambin, entitled "Method For Percutaneous Arthroscopic Disc Removal, Bone Biopsy And Fixation Of the Vertebrae," incorporated herein by reference.

The improved approaches described herein provide for effective, reproducible, efficient and safe procedures for the immobilization of joint, e.g., the SI joint. The procedures are systematic such that less experienced surgeons can effectively perform the procedures with satisfactory outcomes. The use of less invasive procedures can provide for more rapid recovery of the patient and a quicker return to normal activity. Kits can provide a convenient and efficient approach for distributing tools for the performing sacroiliac joint immobilization in either a more open or less invasive/close procedure. The kits can comprise one or more tools and/or sizes of tools for use in a procedure. Closed procedures using nested tools as described herein have been performed on several patients with very successful results and rapid recovery periods based on the limited follow up available to date.

I. Joint Immobilization

Referring to FIG. 1, the SI joint 104 is located between the sacrum 100 at the base of the spine and the ilium 102, the upper bone of the pelvis. Various ligaments support the SI joint 104 by connecting the sacrum 100 and the ilium 102. The extra-articular recess 106 between the sacrum 100 and ilium 102 forms an entrance into the SI joint 104 from the back of the patient. The approach to the SI joint from the back through the extra-articular recess is convenient since significant blood vessels and nerves can be avoided.

Figure 2:
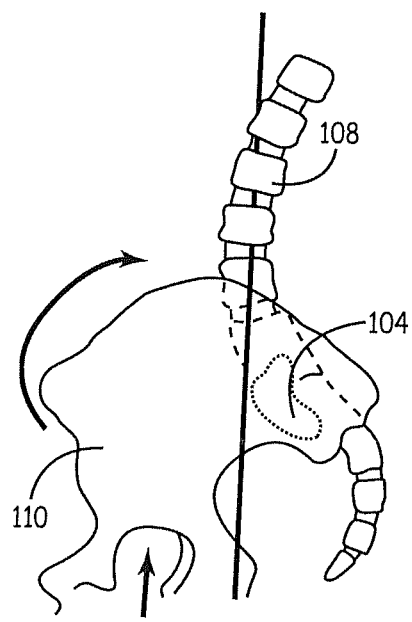
FIG. 2 is a side view of the sacroiliac joint with hidden vertebrae and the sacroiliac joint shown in phantom lines.
Figure 3:
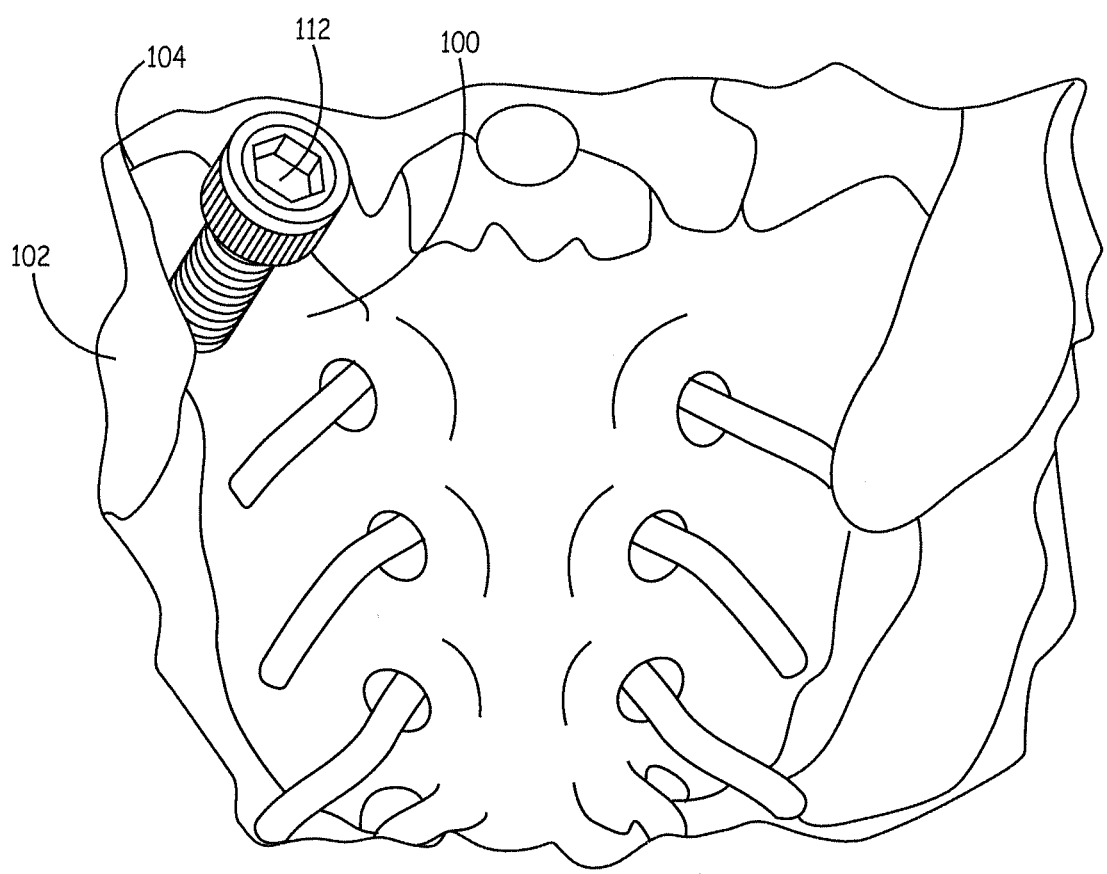
FIG. 3 is a front view of a model of the sacroiliac joint immobilized with a screw.

Referring to FIG. 2, walking and other movement apply torque and translational forces on the SI joint 104. As shown in FIG. 2, SI joint 104 is shown with phantom lines between the spine 108 and the pelvis 110. Ligaments limit the actual movement of the joint. Even with limited movement, these forces on the SI joint can result in pain if there is injury or disease. While the joint looks relatively stable, the SI joint supports the weight of the torso, which is transferred to the legs. Immobilization of the SI joint can relieve pain in appropriate circumstances. FIG. 3 shows schematically immobilization of the SI joint 104 using a simple screw 112. The screw 112 is inserted into the SI joint 104 between the sacrum 100 and the ilium 102 with an approach through the extra-articular recess. Placement of a screw from this orientation through the extra-articular recess into the opening of the joint between the sacrum and the ilium distracts the joint with tension on the supporting ligaments, which has been suggested to provide stable and symptom relieving joint immobilization and possibly fusion upon healing.

The extra-articular region adjacent the SI joint along the patient's back involves a narrowing between the adjacent bones. Thus, the extra-articular recess can itself contribute to the immobilization process as well as fusion from bone growth stimulation and healing. For practical purposes as well as for the discussion herein, the extra-articular region of the SI joint adjacent the joint can be considered part of the joint since it can contribute to immobilization.

While the discussion herein focuses on the SI joint, some of the tools can be used effectively to facilitate procedures on other joints. For example, disc joints are asymmetric with one disc surface being relatively flat and an opposing disc surface being curved. Thus, drilling into the joint between two disks for disc fusion can be advantageously performed using a drill guide that is shifted relative to the center of the joint. Other joints similarly have an asymmetric bone structure at the joint that can advantageously be drilled using the asymmetric drill guides described herein.

II. Tools for Sacroiliac Joint Immobilization

In some embodiments of particular interest, the tools for the sacroiliac joint immobilization are designed for efficient, accurate, safe and less invasive procedures for the immobilization of the joint. However, some of the improved components, combinations and procedures can be used for open procedures as well as in less invasive procedures. Combinations of tools for a particular procedure can be conveniently arranged in a kit such that tools to be used together are available to the physician/health care professional performing the procedure. In addition, the tools can be used to facilitate the delivery of a biological agent to facilitate the beneficial effects of the procedure.

The tools can be generally classified as jigs, nested access tools and implantable elements. Jigs are elements that remain closer to the surface of the patient for alignment and support purposes, and in some embodiments can be used for the relative positioning of multiple implants. The nested tools are used for location of the joint, preparation of the joint for immobilization and for guiding implants and other implantable elements into the joint to contribute to healing and immobilization. Implantable elements refer to mechanical implants and other materials and structures for delivery into the joint to facilitate immobilization.

For the performance of some embodiments of the immobilization procedures, a set of tools can be tracked along an access path according to a nested format to perform the procedure. The tool set generally comprises a set of nested tools that can work cooperatively with jigs, and/or immobilization elements. The nested tool set generally comprises an alignment component (e.g. pins, sizers, depth guides, and the like), a guiding component (e.g. cannulae/tool guides, fillers, and the like), a cutting component (e.g. drill bits/reamers, and the like), and a delivery component (e.g. syringes, inserters, and the like).

A. Nested Tool Set

The tools in the nested tool set cooperate with one another in a nested fashion, which implies that the respective tools can be inserted in a roughly collinear fashion based on a selected position of the joint. The guiding components, cutting components, and delivery components are appropriately sized and cannulated, comprising a channel to enable nesting. The cutting and delivery components are guided into the SI joint by the locations of pins and/or cannulae. In some embodiments, each of the cutting and delivery components comprises a channel for receiving the pin and a diameter that can fit within the channel of the cannula. In some embodiments, the tools of the nested tool set can have cooperating stops to prevent plunging or over penetration.

1. Alignment Components

Alignment components are instruments used to identify the locations at which a passageway is to be created within the SI joint to implant the immobilization elements. A single or a plurality of alignment components can be used in a procedure to provide a single or plurality of implants within the SI joint. Suitable alignment components include, for example, pins and pin guides, e.g. depth guides and sizers.

a. Pins

The pin comprises a shaft with a proximal end and a tip at a distal end. The shaft of the pin can be provided with or without incremental markings to gauge the depth at which the pin is inserted. The tip of the pin can be either blunt or pointed, with a selected degree of sharpness. In some embodiments, the tip, the shaft and/or a portion of the shaft of the pin can be threaded. The shaft and tip can have different or the same cross sectional shape relative to the axis of the pin, such as a circular cross section, oval cross section, rectangular cross section, triangular cross section, or other desired shape. The pin can be formed from a selected combination of these characteristics for the shaft and tip. For example, FIG. 7 shows a pointed pin 510 provided with incremental markings 514, and FIG. 8 shows a blunt pin 520 without incremental markings. In FIG. 7, the distal end 512 of the pin is pointed and sharp. In FIG. 8, the distal end 522 of the pin is generally rounded or ball-shaped, such that it presents a blunt tip.

Pins can be formed from a metal or a metal composite, such as a metal/polymer composite or a metal/ceramic composite, to provide for imaging of pin placement using x-rays or other suitable imaging procedure. In particular, suitable pins can be formed from titanium, stainless steel or other biocompatible metals such as various alloys, such as Nitinol®, a nickel-titanium alloy, used in forming implantable medical components. The pin can have a diameter along the shaft portion from about 1.5 mm to about 4.0 mm, or larger and in further embodiments from about 2.0 mm to about 3.2 mm. A person of ordinary skill in the art will recognize that additional ranges of diameters within the explicit ranges above are contemplated and are within the present disclosure.

b. Depth Guides

Figure 13:
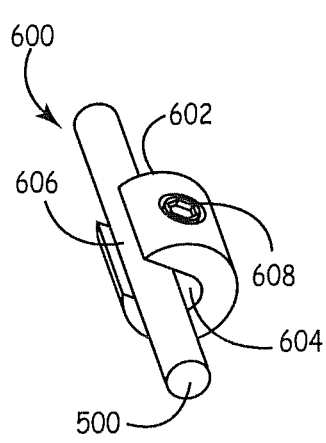
FIG. 13 is a perspective view of a depth guide for attachment to a pin.

A depth guide can prevent over penetration of the pin into the SI joint. While the depth guide can be used to place initial or subsequent pins into the SI joint, the depth guide is particularly useful when placing an initial pin (e.g. blunt pin) into the SI joint. Based on images of the SI joint, the health professional can place a depth guide at a particular place on a pin to prevent accidental over insertion of the pin, which can cause damage to nerves or blood vessels. As shown in FIG. 13, the depth guide 600 comprises a body portion 602 forming a channel 604 that receives the pin 500. The channel is sized to securely grasp the pin yet allow sufficient clearance for sliding the depth guide along the pin. A side opening 606 can be provide access to the channel to allow the pin to be slipped into channel along its body portion instead of inserting one end of the pin into the channel. The body portion comprises a bolt 608 adapted to engage with a hex wrench or other driver for tightening the depth guide onto the pin. Other fasteners, such as a clamp, or bolt configurations can be used to secure the depth guide to the pin at a desired location. The body portion can have various shapes, as desired such that the depth guide does not advance into the incision.

c. Sizers

The sizer provides for estimates for implant sizes as well as centers the pin within the SI joint, and the sizer can be used to guide a replacement pin into the SI joint following removal of an initial pin. By evaluating the size of the joint in the vicinity of an implant, the health professional can select the proper size drill bit and implant with a reduce likelihood of the implant improperly gripping the joint during deployment.

The sizer generally comprises a shaft with a first end and a second end and with a channel extending the length of a shaft that can receive a pin. The first end can comprise a handle, and the second end can comprise a tapered tip, e.g., helical thread. In general, the handle can have any reasonable shape. The shaft can have cross section with a selected shape, such as a circular cross section, oval cross section, rectangular cross section, triangular cross section, or other desired shape. The handle and/or tapered tip can be integral with or reversibly detachable from the shaft. If the handle is removed, additional tools can be placed over the shaft. The reversible attachment of the tip provides for the substitution of different size tips for use with the same shaft and handle. The tapered tip should have a shape that provides for progressive entry into the joint. Suitable tip shapes include a tapered helical shape or other appropriately tapered shape with or without threads.

Figure 14:
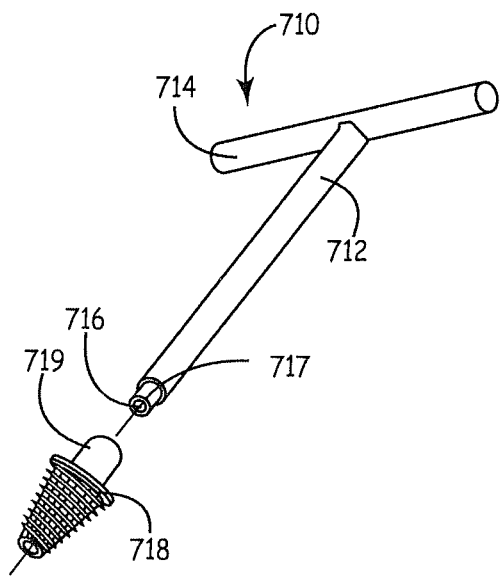
FIG. 14 is a perspective view of a sizer with a detachable handle and a detachable tap.

Referring to FIG. 14, a tubular sizer 710 comprises a shaft 712, a handle 714 and a tapered tip 718. Handle 714 is connected to the first end of shaft 712, and tapered tip 718 is connected to a second end or tip of the shaft. A channel 716 runs throughout the length of the assembled sizer from the tapered tip 718, into the shaft 712, and through the handle 714. In this embodiment, handle 714 forms a "T" with the shaft for gripping and rotating the device by hand. Shaft 712 comprises a first connector element 717 at its second end. Tapered tip 718 has a second connector element 719 and a pointed second end provided with threads in a corkscrew configuration for inserting through the extra-articular recess and into SI joint. First connector element 717 on shaft 712 interfaces with a second connector element 719 on tapered tip 718 to connect the tapered tip onto the shaft for use. First connector element 717 and second connector element 719 can be mated threads, respective elements of a bayonet fastener or other reasonable mated fastener elements to provide for releasable attachment of the tapered tip onto the shaft. A set of tools can comprise tapered tips with different sizes, such as 2, 3, 4 or more different sizes. A particular size tapered tip generally corresponds with a corresponding implant size available for use. In one embodiment, the tools comprise four tapered tip sizes with an approximate range of tapered tip diameter over the length of the tip in the following ranges: 1. 10-13 mm, 2. 12-15 mm, 3. 14-17 mm and 4. 16-19 mm. A person of ordinary skill in the art will recognize that additional ranges of tapered tip diameters within the explicit ranges above are contemplated and are within the present disclosure.

2. Guiding Components

Generally, guiding components include, for example, cannulae used to guide tools, immobilization elements, and/or the like at a site within the SI joint. In some embodiments, cannulae can comprise projections/tangs that extend from the distal end of the cannula for insertion into the joint. Suitable guiding components can also include accessories that help position the cannulae into the joint, such as fillers that internally support the cannula while the cannula is hammered or otherwise driven into place.

Figure 6:
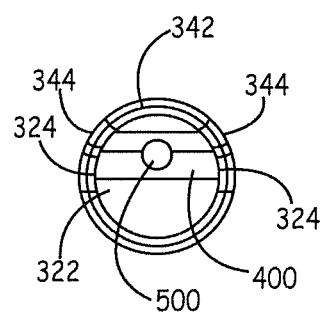
FIG. 6 is a view from the distal end of an assembled nested tool set including a pin, filler, an inner cannula and an outer cannula.

Referring to FIGS. 4-6 a set of nested tools 200 comprises an inner cannula 320 adapted to be inserted within an outer cannula 340 and a cannulated tool 400 adapted to be received within both the outer cannula 340 and inner cannula 320 and inserted over a pin 500. Referring to FIG. 4, the individual tools of the nested tool set are in an exploded configuration with the cannulae cut and pulled apart to expose inner structural relationships. Referring to FIG. 5, the nested tool set of FIG. 4 is in a partially assembled configuration in which a filler 400 is placed within an inner cannula 320 and an outer cannula 340 is partially inserted over the inner cannula with portions of the outer cannula removed for visualization purposes. FIG. 6 shows an end view of the nested tool set in an assembled configuration with the view from the distal tip end.

a. Cannulae/Tool Guides

Cannulae form a passageway for performing subsequent steps of the procedure. The cannula comprises a channel through which a pin and/or sizer already positioned within the SI joint can be received. Thus, the channel can also receive subsequent cannulated cutting and delivery components with such components sliding into the channel. In some embodiments, a cannulated cutting or delivery component can be guided into the SI joint by both the cannula and the pin with a channel of the component receiving a pin while the component is inserted within the channel of the cannula. Although one cannula may be used, two or more nested cannulae, including an outer cannula and an inner cannula, may be used to give flexibility as to the size of tools introduced through the cannulae into the SI joint. In general, the cannulae can be designed for nesting through the use of relatively smooth surfaces along the inner and outer surfaces. In particular, generally the cannulae do not have collars that would interfere with nesting of adjacent cannulae. The cannulae can have inner threads, outer threads, a bayonet connector and/or other fittings or connectors to provide for the attachment of handles, grips or temporary collars to facilitate placement and/or removal of a selected cannula.

Generally, the inner cannula 320 fits or nests within the outer cannula 340. Referring to FIG. 4, each of the inner cannula 320 and outer cannula 340 generally comprises body portions 322, 342, respectively, which form central channels. A plurality of projections/tangs 324, 344 extend from the distal end of the body portion 322 of inner cannula 320 and projections/tangs extend from body portion 342 of outer cannula 340. The tangs extend from a first end positioned at the distal end of the body portion. In general, the shape of the tangs can be selected to fit into the SI joint as guided by a pointed tip. As shown in FIG. 4, tangs 324 are formed through the removal of material from a cylindrical structure such that the tangs follow the natural curves of cannula body portion 322, although in other embodiments, tangs can be welded or otherwise attached to the body portion. Similarly, the tangs can have different shapes, although the effective tip is generally pointed and the edges are appropriate to support the joint.

The projections of the cannulae with tangs generally can have a length from about 0.25 centimeters to about 3.0 centimeters and in further embodiments from about 0.5 centimeters to about 2.0 centimeters. The tangs can have a projected width in a side view from about 3 mm to about 15 mm, and in further embodiments from about 5 mm to about 10 mm. The projected width corresponds approximately with the spacing of the SI joint at the tang once the tang is inserted in the joint. The width "w" is marked in FIG. 9. The joint 330 with the tangs inserted is shown in FIG. 9A. In some embodiments, projections 324, 344 displace the center of the channel of the cannulae differentially to a side, generally toward the ilium, such that cutting occurs toward the harder ilium bone rather than the softer sacrum bone, while preserving more bone of the sacrum. Other corresponding shifts can be selected for other joints. The displacement of the cannulae can be evaluated as the distance from the center point in the joint with the tangs within the joint as noted with a "p" in FIG. 9A relative to the axis corresponding with the center line of the cannula. This relative distance can range, for example, from about 0.5 mm to about 5.0 mm, and in further embodiments from about 1.0 mm to about 3.0 mm. A person of ordinary skill in the art will recognize that additional ranges of dimensions within these explicit ranges are contemplated and are within the present disclosure.

Figure 9:
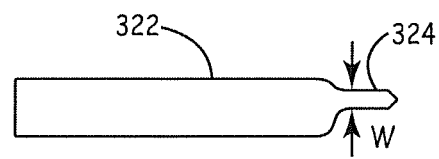
FIG. 9 is a first side view of a cannula with two tangs.
Figure 9A:
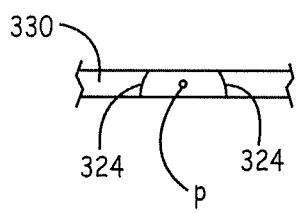
FIG. 9A is a top view into the sacroiliac joint showing a set of inserted tangs into the joint.
Figure 10:
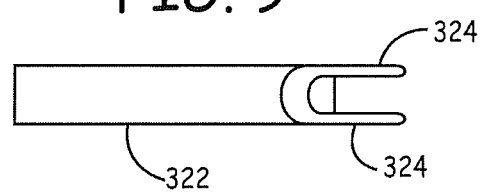
FIG. 10 is a second side view of the cannula of FIG. 9 with the view rotated 90 degrees around the axis of the cannula relative to the view in FIG. 9.

As shown in FIGS. 6, 9, and 10, the projections 324, 344 are asymmetrically distributed relative to the central passage to provide for the displacement of the cannula. Referring to FIG. 6, the projections 324, 344 and cannulated filler 400 are off center relative to the cross sectional shapes formed by the nesting of the inner and outer cannulas 320, 340. In other words, the projections 324, 344 are unevenly spaced around the respective inner 320 and outer 340 cannulae. FIG. 9 shows each of the projections 324, 344 are asymmetrically distributed around the circumference of the cannulae. FIG. 10 shows the gaps formed between the projections 324, 344 are of unequal portions. The different spacings between the tangs on the two sides of the tangs create projections unevenly spaced around the distal end of the body portion of the cannula.

The central passage 322, 342 formed by the inner cannula 320 and outer cannula 340 provides a space for the introduction of appropriate tools to complete the procedure while the walls of the cannula provide protection for the surrounding tissue. In some embodiments, the inner wall of the central passage of each cannula can include a depth stop to align the cannulae and a cutting component relative to one another. The cannula or its distal end can be tapered.

The cannulae can come in a variety of lengths and exterior and interior surface diameters, dependent on the needs of the devices used for the procedure. The cannula generally has an outer diameter of no more than about 2.5 centimeters (cm), and the wall of the cannula can be as thin as suitable with the device having the desired mechanical strength. The dimensions of the cannulae generally are selected to correspond with the set of available implant sizes such that the implants can be appropriately delivered. In some embodiments, a set of implants can have its largest outer diameters being from about 8 to about 30 mm, and one set of six implants have their largest outer diameters being 10, 12, 14, 16, 18 and 20 mm respectively. Corresponding cannulae can have inner diameters from about 8.5 to about 30.5 mm and in an example embodiment with six implant sizes, suitable values of inner diameters are about 10.5, 12.5, 14.5, 16.5, 18.5 and 20.5 mm, although somewhat different clearance values between the cannulae and the implants can be used if desired. The outer diameters of the cannulae can be roughly 1-2 mm greater than the inner diameters. The cannulae have a sufficient length to reach the SI joint and extend outward from the patient's skin. Thus, cannulae can have lengths, for example, from about 9 cm to about 20 cm. A person of ordinary skill in the art will recognize that additional ranges of dimensions within the explicit ranges above are contemplated and are within the present disclosure. With a nested set of cannulae, the cannulae with smaller diameters can have a somewhat longer length since the smaller cannulae can enter the joint a greater distance. The cannulae can have a circular cross section, oval cross section, rectangular cross section or other desired shape that provides the desired channel. The cross sectional shape and size can vary over the length of the cannula.

The cannula provides the passageway for the placement and insertion of the immobilization element, as well as for performing drilling/cutting or other preparatory work for appropriate embodiments. Introduction of various tools, implants and other devices necessary to immobilize a joint, e.g., the sacroiliac joint, are facilitated through the cannulae. Cannulae are typically formed from metals, such as stainless steel, titanium or combinations thereof, metal composites or polymers, such as polyesters.

b. Fillers

Figure 11:
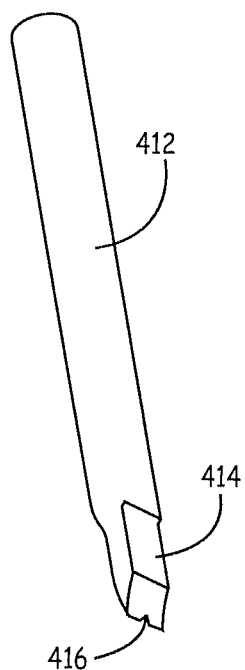
FIG. 11 is a side perspective view of a filler.

A tool with a wedge shaped tip can also be useful to place the cannulae into the joint. The filler can provide support for the cannulae while cannulae are hammered into place to inhibit bending of the cannula or tangs. Referring to FIG. 11, filler 410 comprises a channel 416 that can be inserted over a pin for guiding purposes and a collar 418 that can facilitate removal of the filler. Filler 410 can fill the interior lumen of a cannula with the wedge tip aligning with the tangs of the cannula such that the wedge enters the joint along with the tangs. Thus, the wedge has the same off center displacement of the tangs so that the elements can enter the joint at adjacent points. A mallet or the like can be used to hammer on the filler to drive the filler and the corresponding cannula(e) into the SI joint.

3. Cutting Components

Figure 12:
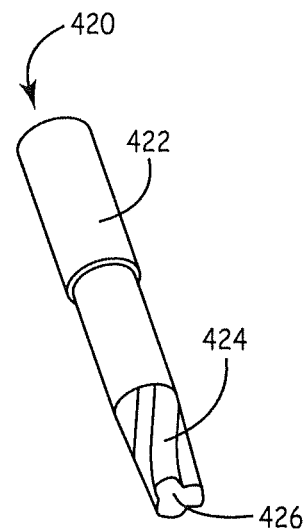
FIG. 12 is a perspective view of a drill bit for use with a nested tool set.

Preparation of the joint can involve opening the joint for the placement of the immobilization element and/or preparation of the bone surface for healing following immobilization. Using the tool guides discussed above, the cutting component can open up a hole or passageway for insertion of an implant and/or implantation material. The cutting components can also be used to remove an implant from the sacroiliac joint. As shown in FIG. 12, suitable cutting components 400 can include, for example, a reamer/drill bit 420. The cutting components 400 generally can be cannulated with a channel for insertion over a pin.

The cutting components can be foamed from suitable metals, such as stainless steel and titanium, although some other hard materials can be used. The cutting elements have an appropriate dimension to prepare the joint for placement of the immobilization element. For less invasive procedures, the elements have a suitable dimension for use through a cannula.

For performing procedures within a cannula, a drill bit generally is used to cut away the bone to create a passageway for the cannula and/or implant. Referring to FIG. 12, a drill bit 420 comprises a shaft 422, a drill bit tip 424, and a channel 426 extending within the cutting tool for receiving a pin. In some embodiments, shaft 422 can comprise inwardly stepped sidewalls defining a plurality of segments with smaller cross-sections from one end of the reamer to the drill bit tip 424. Drill bit 420 can work in conjunction with a drill to provide access to the joint by the immobilization elements. The drill can comprise a manual drill, such as a handle or torque transmitter, or a motorized drill, such as power drills used in the orthopedic arts. The shaft at its largest cross sectional dimension can be generally cylindrical with a diameter slightly less than the inner diameter of the cannula such that the drill bit remains roughly centered during use while still fitting within the cannula.

The drill bit tip 424 at the distal end of the shaft can be comprised of a plurality of flutes, threads, or cutting edges, which assist in the drilling process. In addition, the drill bit can have length markings along the drill bit shaft that assist in determining the depth to which the drill bit has entered the substance being drilled. The proximal end of the drill bit can be adapted to attach to a drill instrument. The drill bit can attach to the drill at the shaft or with a chuck. Drill bits can be formed from a metal or metal composite, and are often formed from stainless steel, titanium or tungsten carbide. The diameter of the drill bit tip is generally slightly less than the diameter of a corresponding immobilization element. The drill bit has a sufficient length for attachment to the drill while reaching into the SI joint.

While the drill and drill bit can be used for inserting the implant, the drill and drill bit can be adapted for removing the implant. The drill bit can have reverse flutes, threads, or cutting edges that thread into and grips the implant and turns the implant in a reverse direction relative to its insertion, to remove the implant.

4. Delivery Components

Generally, delivery components are used to deliver immobilization elements and/or immobilization material into the SI joint. Suitable delivery components include, for example, inserters, syringes, or the like.

a. Inserters

Inserters can be used to place the implant within the SI joint. Inserters can be cannulated, comprising a channel for receiving a pin already positioned within the SI joint. FIG. 20 shows a tubular inserter 900 comprising a shaft 902 with a fitted tip 904. The tip 904 is adapted to receive an implant, and the inserter with the implant is inserted over the pin and into the SI joint. An instrument can be used to slide the implant from the tip of the inserter into the passageway created by the cutting component. The inserter tip 904 can comprise, for example, a clip or notch to snap onto the implant while the implant is being screwed into place to allow the inserter to be disengaged after the implant is inserted into the joint. An inserter for a spinal fusion cage is described further in U.S. Pat. No. 4,961,740 to Ray et al., entitled "V-Thread Fusion Cage and Method of Fusing a Bone Joint," incorporated herein by reference.

b. Syringes

Syringes can be used to place filler material within the SI joint. After the implant is placed into the passageway created by one or more of the cutting components, the existing passageway can be filled with filler material. The syringe can also be inserted over the pin and into the passageway, and the barrel pushed to release the filler material into the joint, e.g. SI joint. FIG. 21 shows a syringe 1000 comprising a barrel 1004 within a body 1002 that has a tip 1006 for directing filler material.

B. Jigs

Jigs can be used to stabilize the incision location through providing a structure that rests on the patient's back or other appropriate location or on other instruments with a hole leading into the site of the procedure. Although a single immobilization element can be implanted within the SI joint, generally multiple immobilization elements are implanted within the SI joint. For inserting multiple immobilization elements within the SI joint, multiple pins are inserted within the SI joint to mark the locations at which the implants are to be inserted. Some jigs facilitate the placement of multiple implants through providing multiple incision sites with a fixed appropriate relative spacing. Suitable jigs and other placement devices include, for example, gunsight spacers, triangular jigs, universal/articulated jigs, and the like.

FIGS. 15-19 show several particular embodiments of jigs. As shown in FIG. 15, a gunsight device 810 for placing multiple pins within the SI joint. The gunsight spacer comprises two tubular portions 812 connected by a connecting bar 814. The connecting bar 814 has a length such that the centers of the proximal openings of the tubular sections are from about 18 millimeters to about 22 millimeters to place implants at a corresponding distance away from each other. Each of the tubular portions comprises a channel 816 that connects with an opening in the connecting bar to receive a pin. The tubular portions have different lengths. The longer tube is placed over a pin at a first implant site to determine the placement of the subsequent pin at a subsequent implant site.

Single site jigs can be used to stabilize the implant site along the patient's back to facilitate performing the procedure. FIGS. 16 and 17 show two different configurations of single site jigs. In FIG. 16, jig 820 comprises a body portion 822 and a removable slug 824. Body portion 822 has three channels 826 near the respective three corners of the body portion, one of which is located in removable slug or bushing 824. The three channels extend from the top surface through the bottom surface of the body portion for the placement of a pin, and the three channels may or may not have the save diameter as each other. Removal of the slug or bushing results in a larger channel 828 through which tools can be introduced to the selected location in the SI joint.

In FIG. 17, the jig 830 comprises a body portion 832 and a slug 834. Jig 830 has two channels 836 near the corners of the body portion extending from the top surface through the bottom surface of the body portion. One of channels 836 pass through removable slug or bushing 834. The two channels 836 may or may not have the same diameter as each other. Removal of the slug or bushing 834 from body portion 832 results in a larger channel 838 through which tools can be introduced to the selected site at the SI joint. The channels or pin holes 826, 836 that do not pass through the slugs 824, 834, respectively, are used for anchoring pins that help to hold the jig in place on the patient. In some embodiments, the anchoring pins can be placed slightly into the ilium with a sharp tip for particular stability. Screws 839 can be used to secure the jig to the anchor pins during the procedure.

FIGS. 18-19 show two different configurations of a jig designed for the placement of multiple implants. Each of the jigs comprises three holes for inserting pins and/or cannulated tools. In FIG. 18, the universal guide 840 comprises a central portion 842, wing portions 844, horizontal axes 845 and vertical axes 847. Wing portions 844 have limited rotational motion in two planes relative to central portion 842. Central portion 842 comprises a channel 846, and wing portions 844 each comprise a channel 846. Channels 846 can be adapted to receive a removable bushing or slug as described with respect to FIGS. 16 and 17 for positioning pins into the SI joint. Removing the bushing or slug opens channels 846, which is suitable for introducing tools into the SI joint. The channels extend from the top surface of the body portion or each of the pieces to the bottom surface of the body portion or each of the pieces.

In FIG. 19, jig 860 comprises three connecting cylindrical tubes with one tube 862 atop two tubes 864. Each of the bottom cylinders connect at one edge with the top cylinder. Cylindrical tubes 862 have a channel 866. Channels 866 can be adapted to receive a bushing or slug, which can have a channel for a pin. With the bushing removed, tubes 862, 864 can provide for delivery of tools wider than pins to a selected location in the SI joint. Jigs with multiple bores for the placement of multiple implants can facilitate and speed the implantation of multiple implants since a single jig needs to be placed and measurements for subsequent implants does not need to be made.

C. Immobilization Elements

The immobilization element can be, for example, bone graft material, titanium metal fragments, a dart, a shim, a wedge, a nail, a screw, or the like, or combinations thereof. The immobilization element can be cannulated. These implants generally can be delivered using the tools and preparation procedures described herein. An improved implant for the sacroiliac joint is a tapered screw. Tapered screws for sacroiliac immobilization/fusion are also described in the present inventor's copending U.S. patent application Ser. No. 10/797,481, filed on Mar. 10, 2004, entitled "Sacroiliac Joint Immobilization," and U.S. patent application Ser. No. 11/879, 536, filed Jul. 17, 2007, entitled "Bone Screws and Particular Applications to Sacroiliac Joint Fusion," both of which are hereby incorporated herein by reference.

In general, the tapered screws can have tapered cores, tapered threads or both. While a taper can increase the incremental displacement of the implant from the tip toward the head, other parameters can similarly increase the thread displacement along the length of the implant. For example, threads can have increased displacement through an increase in thickness that correspondingly increases displacement resulting from increased thread volume.

In general, the implants/screws can be formed from any suitable biocompatible material. The material can be biologically effectively inert or can impart specific desired biological effects, such as through the elution of bone morphogenic protein. Suitable biocompatible materials can include, for example, metals, such as stainless steel, tantalum and titanium, rigid polymers, such as polycarbonates and polyetheretherketone (PEEK), ceramics, such as alumina, or composites, such as carbon composites or carbon fiber composites. In some embodiments, the screws can comprise a bioresorbable polymer, such as poly(hydroxyacids), poly(epsilon-caprolactone), polylactic acid, polyglycolic acid, poly(dimethyl glycolic acid), copolymers thereof and mixtures thereof. The screws can be formed, for example, using conventional machining, molding or the like. The screw or its surface can be porous. For example, porous tantalum is commercially available for forming the screw. In addition, synthetic bone materials and/or sterile bone materials, either allograft or xenograft materials, can be used to form the implantation elements. Suitable synthetic bone material includes, for example, coral and calcium compositions, such as hydroxyapatite, calcium phosphate and calcium sulfate.

In some embodiments, the implant can be formed from a bio-resorbable polymer a natural or synthetic bone material or a combination thereof and a bioactive agent that stimulates bone development, such as BMP. The BMP can be blended with the material prior to molding, casting or otherwise formed into the implant or portion thereof. Generally, if a portion of the implant is formed from the BMP blended with bioresorbably polymer or bone material, this portion can be a support portion, i.e., a portion that provides mechanical integrity to the implant. In appropriate embodiments, as the resorbable polymer biodegrades, bone replaces the implant material. Similarly, for implants formed from the bone material, the implant becomes incorporated into the new bone that forms as a result of the bioactive agent.

Optionally, a bioactive agent can be coated on the surface of the immobilization element. To coat the immobilization device with the bioactive agent, the device can be dipped in a composition comprising the bioactive agent, sprayed with a composition comprising the bioactive agent, painted with the bioactive agent, and/or coated with other processes, such as those generally known in the art. If the coating composition comprises a solvent, the solvent can be allowed to evaporate after applying the coating composition. The bioactive agent can be applied alone as a coating composition or with another agent to control the elution of the agent. The agent can be applied from a solution with a solvent that can evaporate following the application of the coating solution. Also, the bioactive agent can be combined with a control release agent, such as a biodegradable polymer that gradually releases the bioactive agent as the polymer degrades within the patient. Biocompatible, biodegradable polymers are known in the art, such as polylactic acid, poly(glycolic acid) and copolymers and mixtures thereof. A binder may or may not be included to control the elution from the coating. Furthermore, the bioactive agent can be injected or otherwise delivered in the vicinity of the immobilization device. The bioactive agent can be combined with a suitable biocompatible carrier, such as commercially available buffered saline or glycerol.

Suitable biologically active agents include, for example, bone morphogenic protein (BMP) and cytokines. BMP mediates the formation and healing of bone, cartilage, tendon and other bone related tissues. One human BMP polypeptide is described in detail in Published U.S. Patent Application Serial Number 2003/032098 to Young et al., entitled "Bone Morphogenic Protein," incorporated herein by reference. Suitable cytokines include, for example, human chemokine alpha 2, which is effective to stimulate bone marrow growth. A human cytokine, human chemokine alpha 2, is described in U.S. Pat. No. 6,479,633 to Ni et al., entitled "Chemokine Alpha 2," incorporated herein by reference.

III. Procedure for Immobilization and Extraction

A variety of procedures can effectively make use of the tools and immobilization elements described herein. The procedures can be open procedures in which a larger incision is made to move tissue such that the joint is exposed and in view. In some embodiments of particular interest, the procedure is a less invasive procedure performed through a cannula or the like to provide more limited access to the joint through a small incision. Less invasive procedures are desirable since small incisions impose less injury to the patient from the procedure and thus correspondingly can have shorter recovery times. Generally, the tools described herein are designed to facilitate the closed procedures for SI joint immobilization. The procedures are directed to immobilizing the SI joint upon a determination that such a result is indicated. Similar procedures can be performed for removing an implant from the SI joint.

In some embodiments, an immobilization element is placed within the SI joint in contact with adjacent bone to distract the joint and to contribute to joint immobilization. In general, it can be desirable to remove at least a top layer of the bone at the immobilization point prior to immobilization to expose an inner portion of the bone to stimulate the bone healing process that can promote bone formation at or around the immobilization element. This exposure of the bone can be performed using drilling, cutting, scraping or the like using cutting components described above. Biologics, such as bone morphogenic protein, can be used to stimulate bone growth in the vicinity of the procedure, and this bone growth can contribute to fusing of the joint, which corresponds with effectively complete immobilization of the joint.

Less invasive procedures generally involve small incisions generally no more than 4.0 cm in length and in some embodiments no more than 2.5 cm across. One or multiple cuts through the tissue can be performed with scalpels or the like. The procedure can generally be organized in terms of a) locating a selected position in the joint, b) preparing the joint for immobilization and c) placement of immobilization elements. Positioning within the joint can be established using a pin or the like. Once the pin is in position, a jig can be used to stabilize the location along the patient's back in the vicinity of the incision and to facilitate the introductions of instruments into the site. In some embodiments, the jig can facilitate the placement of additional implants relative to an initial implant location.

Based on an image of the site, pins, such as blunt pins, can be inserted to mark the edges of the joint along the patient's back. Based on the location of the marked edges of the joint, a pin can be inserted into the patient for locating the SI joint. A blunt pin can be used to determine the location of the SI joint more safely than the sharp pin since the blunt pin is less susceptible to accidental insertion past the joint, which can result in injury to nerves and/or blood vessels. The position of the pin can be checked with imaging, such as x-ray imaging. In some embodiments, the operating room or a nearby location can be equipped with a CT-scan machine that can image the pin placement relative to the adjacent bones from a wide range of angles. Alternatively or additionally, some operating rooms are equipped with x-ray devices on a moveable arm such that images of the pin can be taken at several selected angles. With a fixed orientation x-ray apparatus, a range of angles can be imaged by moving the patient relative to the apparatus. In this way, the orientation of the pin can be verified with respect to desired placement within the joint.

Figure 22:
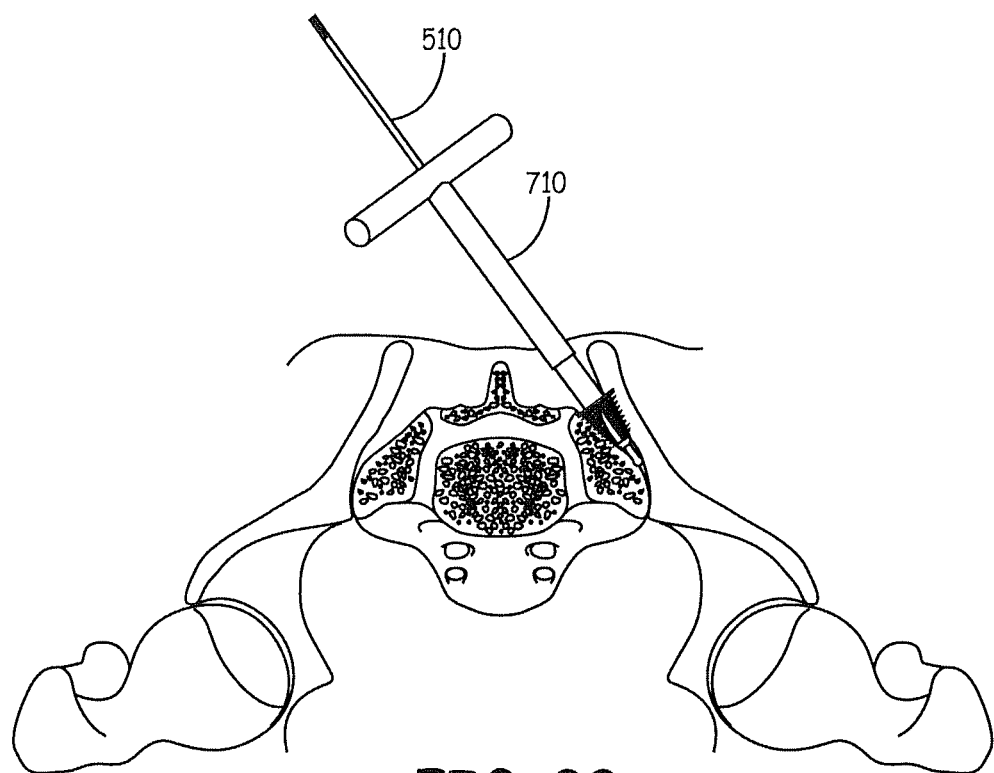
FIG. 22 is a view of a sizer inserted over a blunt pin within the sacroiliac joint.

Although optional, a sizer can be useful for sizing the SI joint and centering the pin. Referring to FIG. 22, a sizer 710 is inserted over the blunt pin 510 and through the extra-articular recess and into the joint. The sizer can be replaced with a different sized sizer if the medical professional determines that the originally selected sizer does not fit into the joint properly. Once a sizer is selected with a proper size to insert a reasonable distance into the joint with a snug feel, the sizer helps orient the pin straight into the joint. Once the pin and sizer are positioned, the sizer can be used to guide cannula (e) into the SI joint by sliding the cannula(e) over the sizer. The positioning of the sizer and pin ensures that the inserted cannula(e) are positioned evenly relative to the pin once the sizer is removed. In some embodiments, with the desired number of cannula(e) inserted, the blunt pin can be removed and replaced with a sharp pin that can safely go further into the joint since the orientation has been confirmed. A depth guide can be used with either or both pins to limit the distance of entry of the pins into the joint. Then, the sizer can be removed. If the cannulae are inserted with the sizer in place, generally a filler is not used, while in alternative embodiments, the cannulae can be inserted with the assistance of a filler if a sizer was removed or not used.

Figure 23:
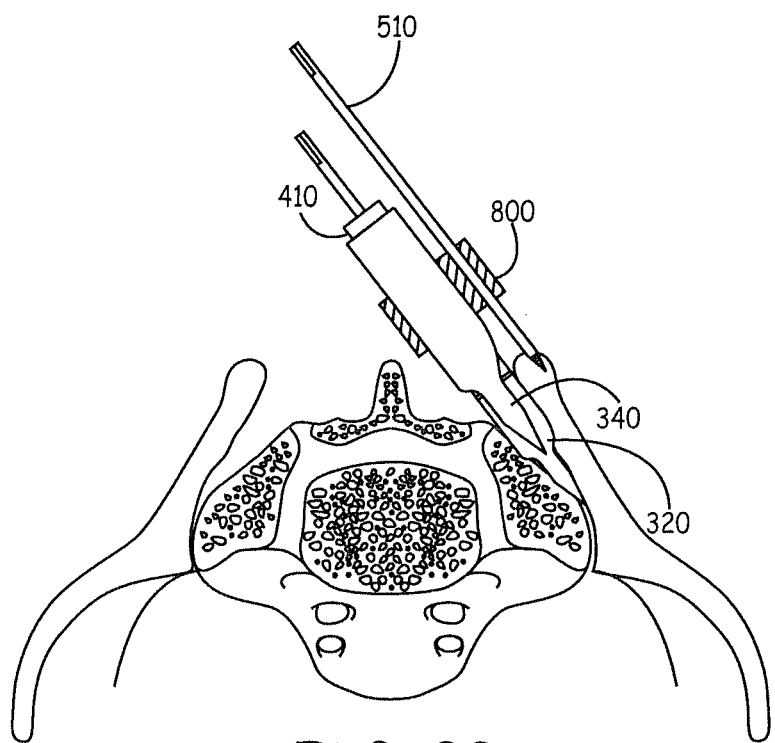
FIG. 23 is a view of a filler being used to support the insertion of cannulae into a sacroiliac joint.
Figure 24:
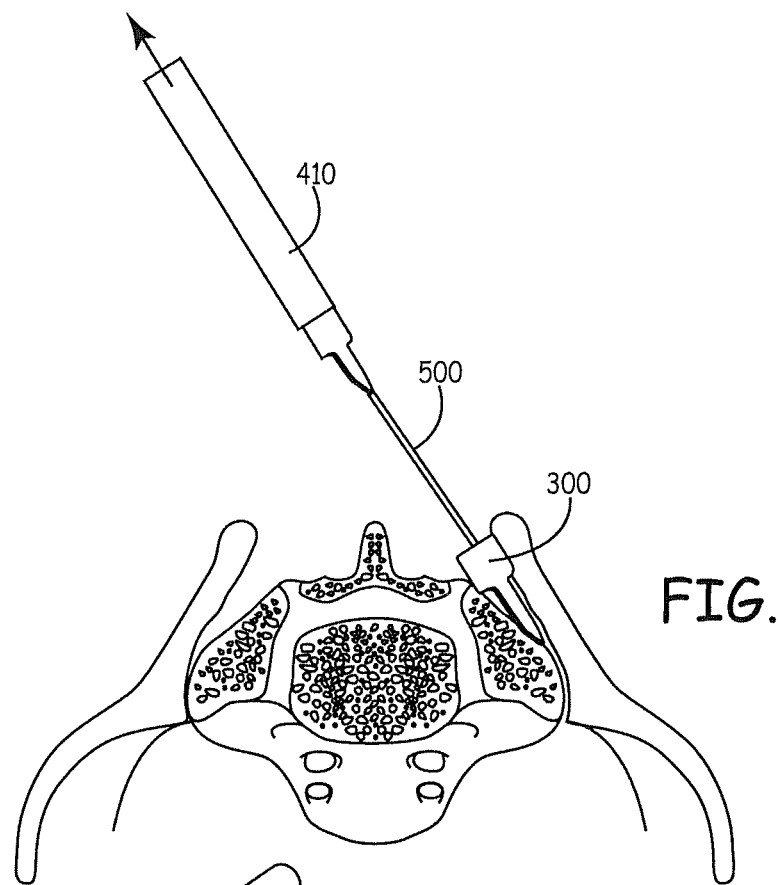
FIG. 24 is a view of a filler being removed from the SI joint after the cannulae are inserted.

Cannula(e) can be placed over the pin and sizer into the SI joint with the help of a filler. The cannulae and filler can be hammered into the joint to anchor a cannula with prongs into the joint. The filler snugly fits within the cannula to support the cannula to prevent bending of the cannula when the cannula is hammered into the joint. Referring to FIG. 23, filler 410 is used to support the cannulae 320,340 while the cannulae are being inserted into the joint. A jig 800 further supports the orientation at which the cannulated tools, and a pin is inserted into the joint with an anchoring pin 510 in the ilium supporting jig 800 relative to the SI joint. Referring to FIG. 24, a filler 410 is removed from the sharp pin 500 and cannula (e) 300, leaving the pin 500 and cannula(e) 300 in place, although a section of the cannula is removed to provide for visualization of the pin.

A plurality of nested cannulae with prongs can be put into place either simultaneously and/or sequentially. In some embodiments, cannulae with tangs or prongs can be used to direct the cannulae toward the ilium and away from the sacrum, such that cutting components inserted within the channel of the cannulae cut into harder ilium bone rather than the softer sacrum bone. More than one cannula can be used to adapt to the various sizes of the cutting components, implants, etc. For example, an inner cannula with tangs and outer cannula with tangs can be used, forming sequentially larger channels around the pin. If more space is needed for a cutting component, implant, or other tool to access the SI joint, the inner cannula with tangs can be removed, leaving an outer cannula with tangs to guide additional tools. This process can be repeated if desired and if there were more than two cannulae placed in the site.

Figure 25:
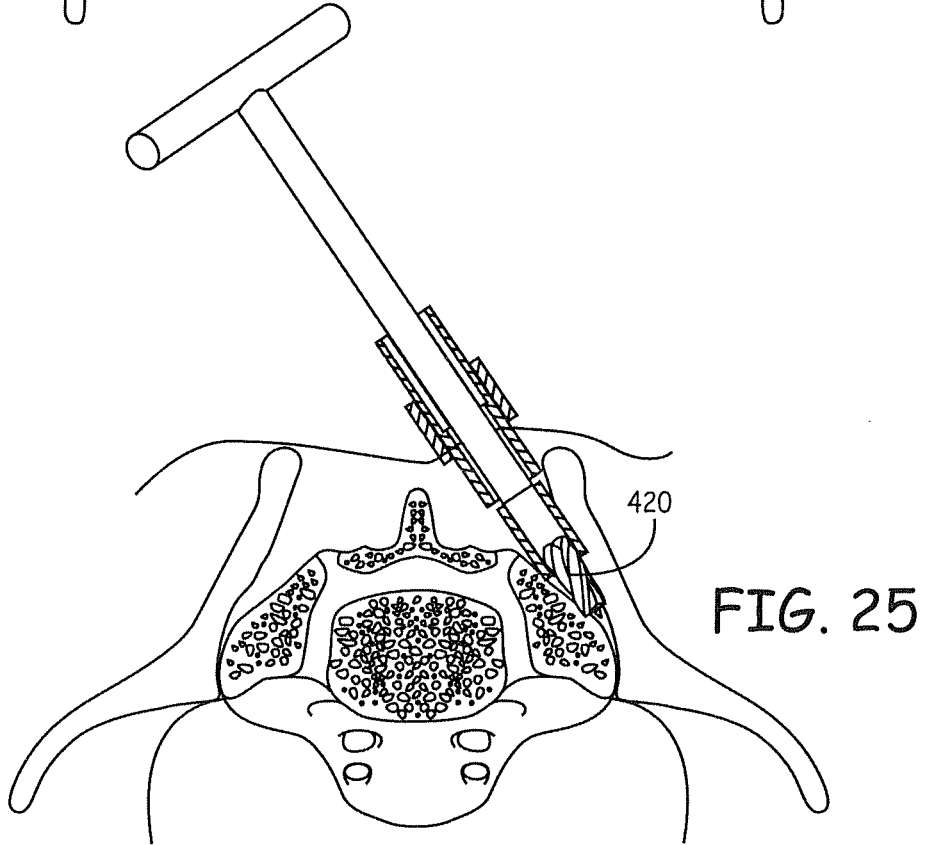
FIG. 25 is a view of a drill bit being used to create a passageway for an implant.

Once the desired number of cannulae is in place, the site can be prepared for inserting the implant and/or filler materials or removal of an implant. For example, a cannulated drill bit, or the like can be used to cut into the bone around the pin position with the pin received within the channel of the cannulated drill element. The drilling procedure prepares a hole or otherwise decorticates the bone around the joint as a site for placement of immobilization elements. Referring to FIG. 25, a drill element 420 is used to create a passageway into the SI joint through which the immobilization element is implanted. The drill element is inserted within the channel(s) of the cannula(e). In some embodiments, the drill bit is inserted over a pin such that the drill bit is guided by both the pin and the cannula, and the drill bit can have a bushing or the like to steady the drill bit within the cannula. A motorized drill can replace a manual drill design if desired.

Figure 26:
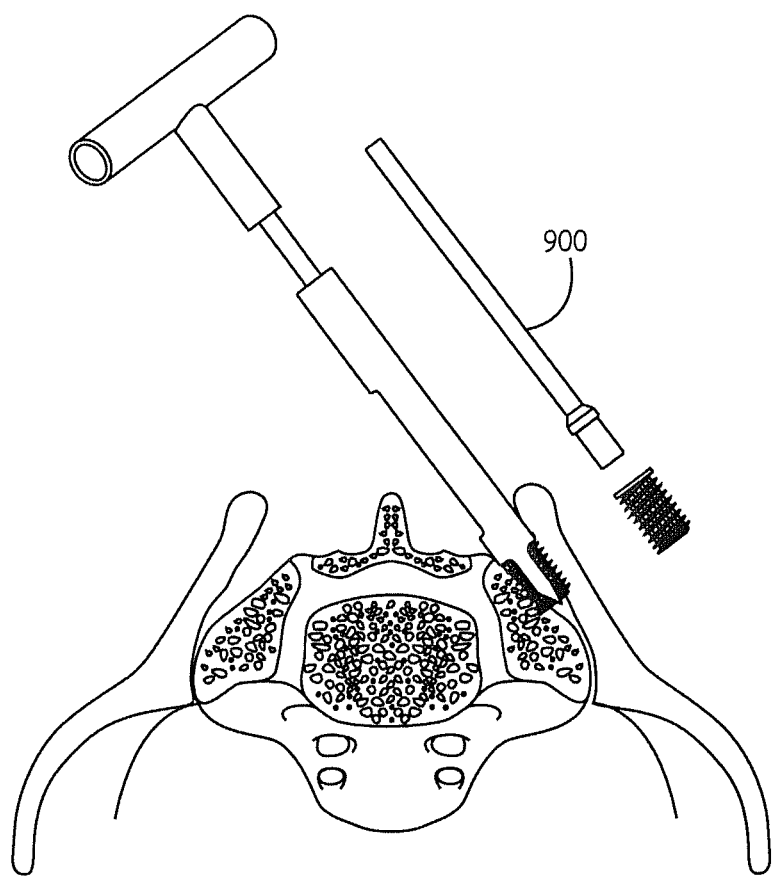
FIG. 26 is a view of an inserter being used to implant the immobilization element into the sacroiliac joint.

The desired immobilization element can then be placed in the SI joint at the pin position such as with an optional cannulated inserter. A cannulated inserter comprises a channel for receiving the positioned pin. If an inserter is not cannulated, the pin can be removed prior to use of the inserter. The cannulated inserter can be releasably attached to an implant for delivery of the implant, and the ensemble can be slid over the pin or otherwise placed into the SI joint through the cannula. Referring to FIG. 26, a cannulated inserter 900 comprises a tip for receiving the immobilization element. The inserter with the immobilization element is inserted within the channel of the cannula(e). The T-handle as described being used with the sizer above can be used with the inserter to help push the inserter through the channel of the cannula (e). Optionally, a syringe with filler material and/or biologics can be inserted over the pin or following removal of the pin, and into the SI joint to apply material into the passageway, such as after the immobilization element is delivered. In some embodiments, the syringe can have a channel for delivery over the pin. Referring to FIG. 21, a needleless syringe comprises a barrel within a cylinder for delivering the filler material. The syringe is delivered through the channel of the cannula(e) with the pin removed. The pin may or may not be removed following the delivery of the immobilization element and/or filler material. In some embodiments, the pin may be cut down if desired. Following deployment of the immobilization element(s) and any additional treatment materials, the incision is then closed.

A series of immobilization elements can be placed along the joint using either an open procedure or a set of less invasive procedures. For example, the series of immobilization elements can be placed in a row in the joint. In this way, two, three, four or more immobilization elements can be placed along the SI joint. The jigs discussed above can be used to place multiple pins and/or cannulated tools into the SI joint.

As for placing the cannulated tools into the SI joint, a jig can have a removable bushing or slug with a channel sized to accept a pin such that a pin can be inserted through the slug with the jig positioned on the patient. The removable bushings or slugs can be removed from the bores of the jigs to provide a bigger bore for the cannulated tools. The jig can be repositioned for additional placement of implants or the jig can have a plurality of channels for the placement of multiple implants through the jig without repositioning.

The procedure described above can be adapted for removing or extracting an implant from a joint, e.g., the SI joint. To perform the removal procedure, a guide pin can be placed within the implant in the joint. Imaging can be used to locate the implant in the joint to guide the insertion of the pin within the implant. A sizer, depth guide, and sharp pin can be used if desired to obtain proper placement of the pin. One or more cannula can be inserted into the joint so the cutting components can accurately access the implant in the joint. For example, a cannulated drill can be used to drill within the cannula and into the implant, gripping the implant and drilling the implant out, such as with a reverse rotation and/or reverse threads relative to the initial rotation for placing the implant into the joint. Alternatively, the cutting components can be used to create a passageway near and/or within the implant, and the cutting components can be used to release the implant. After the implant is removed, a different implant or no implant can be placed in the same or different location. Regardless, the passageway created into the SI joint can be filled with a filler material using a syringe if desired, following removal of the implant.

Packaging

The tools described above can be distributed in a kit for use by a medical professional. Kits provide a convenient and efficient approach to the distribution of equipment for the performance of a selected embodiment of the procedure. Combinations of tools for a particular procedure can be conveniently arranged in a kit such that tools to be used together are available to the physician/health care professional performing the procedure. These tools may be sold individually, as a set with certain selected tools, or together with all the tools. However, selected tools may be sold together as assembled by the manufacture or vendor or selected in a customized fashion by the consumer. For example, the immobilization elements and/or alignment components can be sold as an accessory separately from the kit and from each other.

Generally, the kit can be distributed with the tools in a container. The tools can be sterilized prior to use. The tools are generally reused. Recycled/reusable components are generally formed from a material that can be subjected to an appropriate sterilization approach without damage. Reusable components are generally formed from a material that can be subjected to an appropriate sterilization approach without damage.

Generally, the immobilization elements and/or alignment components are sold separately from the tools and each other. The containers holding immobilization elements can have a sterile interior. The sterilization can be performed by any approach in the art, which can be based, for example, on radiation, chemicals and/or sterile process. Clearly, immobilization elements are generally left with the patient and are not reused.

Each of these kits (e.g. kits with selected tools, kits with alignment components, kits with immobilization elements, etc.) can also include appropriate instructions, warnings, and/or labeling.

The embodiments above are intended to be illustrative and not limiting. Additional embodiments are within the claims. Although the present invention has been described with reference to particular embodiments, workers skilled in the art will recognize that changes may be made in form and detail without departing from the spirit and scope of the invention. The incorporations by reference above are intended to incorporate the full disclosures of the references to the extent that the incorporated subject matter is not inconsistent with the explicit disclosure herein, which will not be altered by any incorporation by reference, as well as to incorporate the disclosures with respect to the specific issues referenced in the incorporation.

What is claimed is:

1. A set of tools for an orthopedic procedure comprising:
   a first pin;
   a first cannula comprising a first end, a second end having a circumference, a substantially cylindrical drill channel extending along a length of the first cannula between the first end and the second end and forming a first opening at the first end and a second opening at the second end, and projections extending substantially similar distances from an edge of the first cannula at the second end and positioned along the circumference of the second opening wherein each of the projections have a first edge and a second edge that have a projected width between the first and second edges and are aligned for the respective first edges to engage one side of a joint and the second edges aligned to engage an opposite side of the joint when the projections are inserted into the joint with a body portion of the first cannula remains extending outward from the joint and wherein the projections are asymmetrically distributed around the drill channel of the first cannula;
   a first sizer comprising:
      a shaft having a shaft bore that has a size to receive the first pin and an outer surface that fits within the drill channel of the first cannula, and
      a tapered tip secured to the shaft of the first sizer, the tapered tip having an outer surface that fits within the drill channel of the first cannula and having a tip bore that has a size to receive the first pin and aligned with the shaft bore of the first sizer; and
   a drill bit comprising a shaft having a conduit for receiving the first pin, a tip with cutting flutes and an outer surface that fits within the drill channel of the first cannula.

2. The set of tools of claim 1 further comprising a positioning guide comprising a plurality of channels with a size to accept the first cannula and a plurality of bores each sized to receive a pin wherein a relative position of the plurality of channels provides for sequential placement of implants.

3. The set of tools of claim 1 further comprising a depth guide comprising a body with a conduit for receiving the first pin and a fastener for fastening the depth guide to the first pin at a selected position along the first pin.

4. The set of tools of claim 1 wherein the shaft of the first sizer comprises a first end and a second end, a handle releasably attached to the first end of the shaft of the first sizer and the tapered tip attached to the second end of the shaft of the first sizer.

5. The set of tool of claim 1 wherein the shaft of the drill bit comprises a section with a wider diameter relative to the tip of the drill bit where the wider diameter is sized to fit within the drill channel of the first cannula.

6. The set of tools of claim 1 wherein the first pin comprises a blunt tip and a diameter along a shaft of the first pin and the set of tools further comprising a second pin with a diameter approximately equal to the diameter of the first pin and with a sharp tip.

7. The set of tools of claim 1 wherein insertion of the projections into the joint displaces the drill channel having a center relative to the joint such that the center of the channel is not centered over the joint.

8. The set of tools of claim 1 further comprising a cannulated inserter having an outer surface that fits within the drill channel of the first cannula.

9. The set of tools of claim 8 wherein the cannulated inserter comprises a first end configured for releasable attachment to an immobilization element.

10. The set of tools of claim 3 wherein the fastener is a clamp or a bolt.

11. The set of tools of claim 1 wherein the drill bit comprises length markings along the drill bit shaft.

12. The set of tools of claim 1 wherein the first sizer tip is releasably secured to the shaft of the first sizer.

13. The tool set of claim 1 comprising an implant for placement into a sacroiliac joint of a human patient, the implant comprising
   a core having threads spiraling around the core,
   a channel extending through the core and sized to receive the first pin, and
   an outer surface sized to fit within the drill channel of the first cannula and to fit securely into the sacroiliac joint following drilling with the drill bit and sizing with the first sizer.

14. The set of tools of claim 1 comprising:
   one or more additional cannula having a selected set of sizes different from the first cannula, each of the one or more additional cannula comprising a first end, a second end, a substantially cylindrical drill channel extending along a length of the one or more additional cannula between the first end and the second end and forming a first opening at the first end and a second opening at the second end wherein the different sized cannula have corresponding different drill channel diameters from each other, and projections extending from an edge of the one or more additional cannula at the second end, each projection comprising a first edge and an opposite second edge and positioned along the circumference of the second opening to support a first side of a joint on the first edges and an opposite side of the joint on the second edges when the projections are inserted into the joint;
   one or more additional sizers, each of the one or more additional sizer comprising a shaft having a shaft bore that has a size to receive the first pin, and an outer surface that fits within the drill channel of a corresponding cannula, and
      a tapered tip secured to the shaft of the one or more additional sizer, the tapered tip having an outer surface that fits within the drill channel of the corresponding cannula and having a tip bore that has a size to receive the first pin and aligned with the shaft bore of the one or more additional sizer.

15. The tool set of claim 14 comprising a corresponding set of implants for placement into a sacroiliac joint of a human patient, each implant comprising:
- a core having threads spiraling around the core,
- a channel extending through the core and sized to receive the first pin, and
- an outer surface sized to fit within the drill channel of the corresponding cannula and to fit securely into the sacroiliac joint following drilling with the drill bit and sizing with the first sizer.

16. A set of tools for an orthopedic procedure comprising:
a first pin;
a first cannula comprising a first end, a second end having a circumference, a substantially cylindrical drill channel extending along a length of the first cannula between the first end and the second end and forming a first opening at the first end and a second opening at the second end, and projections extending substantially similar distances from an edge of the first cannula at the second end and positioned along the circumference of the second opening;
a first sizer comprising:
- a shaft having a shaft bore that has a size to receive the first pin and an outer surface that fits within the drill channel of the first cannula, and
- a tapered tip secured to the shaft of the first sizer, the tapered tip having an outer surface that fits within the drill channel of the first cannula and having a tip bore that has a size to receive the first pin and aligned with the shaft bore of the first sizer;

a drill bit comprising a shaft having a conduit for receiving the first pin, a tip with cutting flutes and an outer surface that fits within the drill channel of the first cannula;
one or more additional cannula having a selected set of sizes different from the first cannula, each cannula comprising a first end, a second end, a substantially cylindrical drill channel extending along a length of the cannula between the first end and the second end and the second end and forming a first opening at the first end and a second opening at the second end wherein the different sized one or more additional cannula have corresponding different drill channel diameters from each other, and projections extending from an edge of the one or more additional cannula at the second end, each projection comprising a first edge and an opposite second edge and positioned along the circumference of the second opening to support a first side of a joint on the first edges and an opposite side of the joint on the second edges when the projections are inserted into the joint; and
one or more additional sizers, each of the one or more additional sizer comprising a shaft having a shaft bore that has a size to receive the first pin, and an outer surface that fits within the drill channel of a corresponding cannula, and
a tapered tip secured to the shaft of the one or more additional sizer, the tapered tip having an outer surface that fits within the drill channel of the corresponding cannula and having a tip bore that has a size to receive the first pin and aligned with the shaft bore of the one or more additional sizer.

17. The tool set of claim 16 comprising a corresponding set of implants for placement into a sacroiliac joint of a human patient, each implant comprising:
- a core having threads spiraling around the core,
- a channel extending through the core and sized to receive the first pin, and
- an outer surface sized to fit within the drill channel of the corresponding cannula and to fit securely into the sacroiliac joint following drilling with the drill bit and sizing with the first sizer.

18. The set of tools of claim 16 wherein the projections are asymmetrically distributed around the drill channel of each cannula and wherein insertion of the projections into the joint displaces the drill channel having a center relative to the joint such that the center of the channel is not centered over the joint.

19. The set of tools of claim 16 further comprising a first cannulated inserter having an outer surface that fits within the drill channel of first cannula wherein the first cannulated inserter comprises a first end configured for releasable attachment to a first immobilization element, and a second cannulated inserter having an outer surface that fits within the drill channel of the one or more additional cannula wherein the second cannulated inserter comprises a first end configured for releasable attachment to a second immobilization element.

20. The set of tools of claim 16 wherein the first pin comprises a blunt tip and a diameter along a shaft of the first pin and the set of tools further comprising a second pin with a diameter approximately equal to the diameter of the first pin and with a sharp tip.

* * * * *

UNITED STATES PATENT AND TRADEMARK OFFICE
CERTIFICATE OF CORRECTION

PATENT NO.          : 9,314,232 B2
APPLICATION NO.     : 13/529123
DATED               : April 19, 2016
INVENTOR(S)         : John G. Stark Page 1 of 1

It is certified that error appears in the above-identified patent and that said Letters Patent is hereby corrected as shown below:

In the Claims:

Column 23, claim 16, line 38 please delete "and the second end".

Column 24, claim 19, line 33 after "of" insert --the--.

Signed and Sealed this
Nineteenth Day of July, 2016

Michelle K. Lee
*Director of the United States Patent and Trademark Office*